US005500230A

United States Patent [19]
Nathanson

[11] Patent Number: 5,500,230
[45] Date of Patent: Mar. 19, 1996

[54] METHOD FOR TREATMENT OF GLAUCOMA WITH NITROGEN CONTAINING GUANYLATE CYCLASE ACTIVATORS

[75] Inventor: James A. Nathanson, Wellesley, Mass.

[73] Assignee: The General Hospital Corporation, Boston, Mass.

[21] Appl. No.: 43,979

[22] Filed: Apr. 7, 1993

Related U.S. Application Data

[63] Continuation of Ser. No. 702,855, Nov. 21, 1990, abandoned, which is a continuation of Ser. No. 147,324, Jan. 22, 1988, abandoned, which is a continuation-in-part of Ser. No. 6,405, Jan. 23, 1987, abandoned.

[51] Int. Cl.$^6$ .......................... A61K 33/38; A61K 31/50; A61K 31/505
[52] U.S. Cl. .......................... 424/619; 514/252; 514/257; 514/913
[58] Field of Search .................................. 514/256, 259, 514/275, 912, 913; 424/606, 600, 619

[56] References Cited

U.S. PATENT DOCUMENTS

| | | | |
|---|---|---|---|
| 3,843,782 | 10/1974 | Krezanoski et al. | 424/679 |
| 4,396,625 | 8/1983 | Yamamori et al. | 514/369 |
| 4,425,345 | 1/1984 | Horlington et al. | 514/913 |
| 4,425,346 | 1/1984 | Horlington | 514/249 |
| 4,477,466 | 10/1984 | Shepard | 514/913 |
| 4,496,544 | 1/1985 | Needleman | 514/13 |
| 4,508,712 | 4/1985 | Needleman | 514/11 |
| 4,532,135 | 7/1985 | Edwards | 514/259 |
| 4,590,207 | 5/1986 | Tomiuga et al. | 514/913 |
| 4,668,506 | 5/1987 | Bawa | 514/913 |
| 4,696,932 | 9/1987 | Jacobson et al. | 514/263 |
| 4,771,059 | 9/1988 | Bodor | 514/357 |
| 4,783,444 | 11/1988 | Watkins et al. | 514/913 |
| 4,826,879 | 5/1989 | Yamamoto et al. | 514/913 |
| 4,861,755 | 8/1989 | Breiphol et al. | 514/11 |
| 4,912,111 | 3/1990 | Sank et al. | 514/256 |

FOREIGN PATENT DOCUMENTS

| | | |
|---|---|---|
| 0231752 | 8/1987 | European Pat. Off. |
| 85/04872 | 11/1985 | WIPO |

OTHER PUBLICATIONS

Antunes–Rodrigues, J. et al., Atrial natriuretic factor inhibits dehydration– and angiotensin II–induced water intake in the conscious, unrestrained rat, *Proc. Natl. Acad. Sci. USA* 82:8720–8723 (Dec. 1985).

Bergey, J. L. et al., Effects of Atriopeptins I, II And III On Atrial Contractility, Sinus Nodal Rate (Guinea Pig) And Agonist–Induced Tension In Rabbit Aortic Strips, *Eur. J. Pharmacol.* 110:277–281 (1985).

Bianchi, C. et al., Localization and characterization of specific receptors for atrial natriuretic factor in the ciliary processes of the eye, *Current Eye Research* 5(4):283–293 (1986).

Bianchi, C. et al., Radioautographic Localization of $^{125}$I–Atrial Natriuretic Factor Binding Sites in the Brain, *Neuroendocrinol.* 44:365–372 (1986).

Cantin, M. et al., The Heart and the Atrial Natriuretic Factor, *Endocrine Reviews* 6(2):107–127 (1985).

Cloix, J. F. et al., Recent Advances On Endogenous Na$^+$, K$^+$–ATPase Inhibitors: Clinical Investigation and Purification, *Clin. and Exper.–Theory and Practice A7 (5&6):* 663–672 (1985).

de Bold, A. J., Atrial Natriuretic Factor: A Hormone Produced by the Heart, *Science* 230:767–770 (Nov. 15, 1985).

Debowska–Weissowa, J. et al., Influence of Nitroglycerine On The Level of Intraocular Pressure, *Klin. Oczna* 88:153–154 (1986).

Erne, P. et al., Vasodilating Agents and Platelet Function: Intracellular Free Calcium Concentration, Cyclic Nucleotides, and Shape–Change Response, *J. Cardiovasc. Pharmacol.* 8 (Suppl. 8):S102–S106 (1986).

Fiink, E. B., Heavy Metal Poisoning, in Beeson, P. B. et al., eds., *Cecil Textbook of Medicine*, Fifteenth Edition, Vol. 1, W. B. Saunders Co., Philadelphia, pp. 76–82 (1979).

Fitts, D. A. et al., Diuresis and Reduction of Salt Appetite by Lateral Ventricular Infusions of Atriopeptin II, *Brain Res.* 348:118–124 (1985).

Focosi, F. et al., Glyceral Trinitrate And Intraocular Pressure: A Tonographic Study In Man, *Annali di Ottalmologia e Clinica Oculistica CXII* (5):361–367 (1986).

Fransen, L. et al., Neonatal opthalmia in the developing world: Epidemiology, etiology, management and control, *Int. Opthalmol.* 11:189–196 (1988).

Gibson, T. R. et al, Autoradiographic Localization and Characterization of Atrial Natriuretic Peptide Binding Sites in the Rat Central Nervous System and Adrenal Gland, *J. Neurosci.* 6(7):2004–2011 (Jul. 1986).

Golden, B. et al., Intraocular Infections, in Hoeprich, P. D., ed., *Infectious Diseases*, pp. 1259–1262, (1972).

Goodman et al., Vasodilators, *The Pharmacological Basis of Therapeutics*, 7th Edition, MacMillan Publishing Company, N.Y., pp. 795–798 (1986).

Kostyuchenkov, V. N. et al., Effect of adreno– and sympatholytic agents on opthalmotonus, *Chem. Abstracts* 76:11, Abstract No. 110e (1972).

Krupin, T. et al., Increased intraocular pressure following topical azide or nitroprusside, *Invest. Opthalmol. Vis. Sci.* 16 (11): 1002–1007 (Nov. 1977).

Krupin, T. et al., Topical vanadate lowers intraocular pressure in rabbits, *Invest. Opthalmol. Vis. Sci.* 19 (11): 1360–1363 (Nov. 1980).

Lide, D. R., ed., *CRC Handbook of Chemistry and Physics*, 72nd Edition, CRC Press, Inc., pp. 4–48, 4–70, 4–72, 4–88, (List continued on next page.)

Primary Examiner—Zohreh Fay
Attorney, Agent, or Firm—Sterne, Kessler, Goldstein & Fox

[57] ABSTRACT

The present invention relates to a method of treating cranial fluid volume dysfunctions such as glaucoma in an individual, comprising administering compounds which effect an increase in cyclic GMP at the site of the dysfunction or at the site of synthesis or removal of the accumulating fluid. In particular, the method of treatment involves the topical use of hydralazine, non-organic nitrites or nitroglycerine, and the systematic use of hydralazine or non-organic nitrites.

14 Claims, 18 Drawing Sheets

OTHER PUBLICATIONS

4–99, 4–103 (1991–1992).

Lynch, D. R. et al., Atrial natriuretic factor receptors in rat kidney, adrenal gland, and brain: Autoradiographic localization and fluid balance dependent changes, *Proc. Natl. Acad. Sci. USA* 83:3357–3361 (May 1986).

Masotto, C. et al., Inhibition of Spontaneous or Angiotensin II–Stimulated Water Intake by Atrial Natriuretic Factor, *Brain Res. Bull.* 15:523–526 (1985).

Masuda, A. et al., Effect of hypotension induced by trimethaphan and nitroglycerine on intraocular pressure in man, *Jap. J. Anesthesiol.* 32:213–216 (1983).

Mittag, T. W. et al., Atrial natriuretic peptide (ANP), guanylate cyclase, and intraocular pressure in the rabbit eye, *Current Eye Research* 6 (10):1189–1196 (1987).

Mutschler, E., Sonstige Vasodilatatoren met direktem Angriff an der glatten Muskulatur, *Arzneimittelwirkungen*, Wissenschaftliche Verlagsgesellschaft, Stuttgart, pp. 461–462 (1986).

Napier, M. A. et al., Specific membrane receptors for atrial natriuretic factor in renal and vascular tissues, *Proc. Natl. Acad. Sci. USA* 81:5946–5950 (Oct. 1984).

Nathanson, J. A., Atriopeptin–Activated Guanylate Cyclase in the Anterior Segment, *Invest. Opthalmol. Vis. Sci.* 28:1357–1364 (Aug. 1987).

Nathanson, J. A. et al., "Second Messengers"in the Brain, *Sci. Amer.* 237:108–119 (1977).

Nathanson, J. A., Nitrovasodilators as a New Class of Ocular Hypotensive Agents, *J. Pharmacol. and Exp. Therap.* 260(3):956–965 (1992).

Needleman, P. et al., Drugs Used for the Treatment of Angina: Organic Nitrates, Calcium Channel Blockers, and β–Adrenergic Antagonists, in Goodman et al., *The Pharmacological Basis of Therapeutics*, pp. 806–816, 1985.

Physician's Desk Reference, 38th Edition, p. 1033 (1984).

Saman, K. et al., Nitroglycerin A Glaukom, *Cs. Oftalmologie* 31: 434–439 (1975).

Samson, W. K. Dehydration–Induced Alterations In Rat Brain Vasopressin And Atrial Natriuretic Factor Immunoreactivity, *Endocrinol.* 117 (3): 1279–1281 (1985).

Sasaki, T. et al., The Effect of α–Human Atrial Natriuretic Polypeptides (α–hANP) on Intraocular Pressure in Albino Rabbits. First Report: In Albino Rabbits with Normal Intraocular Pressure, *Nippon Ganka Gakki Zasshi* 90 (10):1232–1234 (1986).

Scarpelli, P. T. et al., Malignant Hypertension. Evaluation by Fluoroscopic Retinography of the Long–Term Effects of Antihypertensive Treatment on Eyeground changes, *Giorn. Gerontol.* 24:845–858 (1976).

Standaert, D. G. et al., Atriopeptin: potent hormone and potential neuromediator, *Trends in Neurosciences* 8:509–511 (Dec. 1985).

Steardo, L. et al., Brain Barrier Tissues: End Organs for Atriopeptins, *Science* 235:470–473 (Jan. 23, 1987).

Sugrue, F. F. et al., Synthetic atrial natriuretic factor lowers rabbit intraocular pressure, *Eur. J. Pharmacol.* 130:349–350 (1986).

Thulesius, O., Cardiovascular Pharmacology of Molsidomine, *Biblthca Cardiol.* 38: 234–243 (1984).

Tomiuga, T. et al., Effects of Organic Nitrates on Intraocular Pressure in Rabbits, *Atarashii Ganka* 2 (4): (1985).

Waldman, S. A. et al., Atrial Natriuretic Factor Selectively Activates Particulate Guanylate Cyclase and Elevates Cyclic GMP in Rat Tissues, *J. Biol. Chem.* 259 (23):14332–14334 (Dec. 10, 1984).

Whitworth, C. C. et al., Use of Nitrate and Nitrite Vasodilators by Glaucomatous Patients, *Arch. Opthalmol.* 71:492–496 (Apr. 1964).

Wilensky, J. T. et al., Acute Systemic Hypertension After Conjunctival Instillation of Phenylephrine Hydrochloride, *Am. J. Opthalmol.* 76 (1):156–157 (1973).

Windholz, M. et al., eds., Sodium Nitrite, *The Merck Index*, Tenth Edition, Merck & Co., Inc., Rahway, N.J., p. 1238 (1983).

Winquist, R. J. et al., Atrial natriuretic factor elicits and endothelium–independent relaxation and activates particulate guanylate cyclase in vascular smooth muscle, *Proc. Natl. Acad. Sci. USA* 81:7661–7664 (Dec. 1984).Winquist, R. J. et al., Characterization of Synthetic Atrial Natriuretic Factor: Vasodilator Profile and Decreased Vascular Sensitivity in Hypertensive Rats, *J. Hypertension* 2 (Suppl. 3):325–327 (1984).

Winquist, R. J. et al., Possible mechanisms underlying the vasorelaxant response to atrial natriuretic factor, *Fed. Proc.* 45(9):2371–2375 (Aug. 1986).

Winquist, R. J. et al., The Relaxant Effects Of Atrial Natriuretic Factor on Vascular Smooth Muscle, *Life Sciences* 37:1081–1087 (1985).

Winquist, R. J. et al., Vasodilator Profile of Synthetic Atrial Natriuretic Factor, *Eur. J. Pharmacol.* 102:169–173 (1984).

Wizemann, A. et al., Untersuchungen zur ambulanten und perioperativen Augeninnendrucksenkung mit organischen Nitraten, *Klin. Mbl. Augenheilk.* 11:292–295 (1980).

Wizemann, A. J. S. et al., Organic Nitrate Therapy in Glaucoma, *Am. J. Opthalmol.* 90:106–109 (1980).

Woodward, D. F. et al., Sustained Decreases in Systemic Blood Pressure Do Not Cause Ocular Hypotension, *Opthalmic Res.* 21:37–43 (1989).

Zalta, A. H. et al., The Effect of Nitroglycerin Ointment on the External Ocular Structures of Rabbits, *J. Ocular Pharmacol.* 1(1):71–77 (1985).

Grant, J., ed., *Hackh's Chemical Dictionary*, Fourth Edition, McGraw–Hill Book Company, New York, p. 457, (1969).

Hollyfield, J. G., Drug induced photoreceptor degeneration: simulation of inherited degenerative disorders in normal retinas, *Chemical Abstracts* 99, Abstract No. 36790r (1982).

Kobayashi, K. et al., Cerebral metabolism in rat experimental hydrocephalus. Changes in concentrations of ATP and cyclic nucleotides in the brain tissue, *Chemical Abstracts* 103:321–322, Abstract No. 194381p (1985).

Linkewich, J. A. et al., Bradycardia and Congestive Heart Failure Associated with Ocular Timolol Maleate, *Am. J. Hosp. Pharm.* 38:699–701 (May 1981).

Nippon Camphor Co., Ltd., Pharmaceuticals for regulation of brain metabolism and lowering intracranial pressure, *Chemical Abstracts* 94, Abstract No. 90352j (1981).

Owman, C. et al,. Influence of various intracranial pressure levels on the concentration of certain arylethlamines in rabbit brain, *Chemical Abstracts* 75:96–97, Abstract No. 116745z (1971).

Sakabe, T. et al., The relationship between cerebrospinal fluid pressure changes and cerebral blood flow, during anesthesia and the administration of vasodilating drugs, *Chemical Abstracts* 100:22, Abstract No. 114601k (1984).

Tsutsumi, K. et al., α–Atrial natriuretic peptide binding sites in the rat choroid plexus are increased in the presence of hydrocephalus, *Chemical Abstracts* 108:162–163, Abstract No. 180981a (1988).

Williams, D. S. et al., Photoreceptor degeneration in a pure–cone retina. Effects of cyclic nucleotides, and inhibitors of phosphodiesterase and protein sytnesis, *Chemical Abstracts* 107, Abstract No. 131994c (1987).
Cantin, M., et al., *Endocrine Rev.*, 6:107–127 (1985).
de Bold, A. J., *Science*, 230:767–770 (1985).
Winquist, R. J., *Life Sci.*, 37:1081–1087 (1985).
Waldman, S. A., et al., *J. Biol. Chem.*, 259:14332–14334 (1984).
Winquist, R. J. et al., *Proc. Natl. Acad. Sci. USA*, 81:7661–7664 (1984).
Gibson, T. R., et al., *J. Neurosci.*, 6:2004–2011 (1986).
Nathanson, J. A., et al., *Sci. Amer.*, 237:108–119 (1977).
Bianchi, C., et al., *Current Eye Res.*, 5:283–293 (1986).
Samson, W. K., *Endocrinology*, 117:1279–1281 (1985).
Antunes–Rodrigues, J., et al., *Proc. Natl. Acad. Sci. USA*, 82:8720–8723 (1985).
Fitts, D. A., et al., *Brain Res.*, 348:118–124 (1985).
Standaert, D. G., et al., *Trends in Neurosci.*, 8:509–511 (1985).
Lynch, D. R., et al., *Proc. Natl. Acad. Sci. USA*, 83:3357–3361 (1986).
Masotto, C., et al., *Brain Res. Bulletin*, 15:523–526 (1985).
Sugrue, M. F., et al., *Eur. J. Pharmacol.*, 130:349–350 (1986).
Bianchi, C., et al., *Neuroendocrin.*, 44:365–372 (1986).
Wizemann, A. J. S., et al., *Amer. J. Opthalmol.* 90:106–109 (1980).
Masuda, A., et al., *Jap. J. Anesthesiol.* 32:213–216 (1983).
Wizemann, A., et al., *Klin. Mbl. Augenheilk*, 177:292–295 (1980).
Sasaki, T., et al., *Nippon Ganka Gakki Zasshi*, 90: 1232–1234 (1986).
Krupin, T., et al., *Invest. Ophthalmol. Visual. Sci.*, 16:1002–1007 (1977).
Debowska–Weissowa, J., et al., *Klin. Oczna*, 88: 153–154 (1986).
Saman, K., et al., *Cs. Oftalmologie*, 31:434–439 (1975).
Whitworth, C. G., et al., *Arch. Ophthalmol.*, 71:492–496 (1964).
Winquist, R. J., *Fed. Proc.*, 45:2371–2375 (1986).
Medline Abstract of Glaucoma: Et, Ethiology. 1974 IUA.
Embase Abstract 80 118449 (1979).
Chem. Abs., vol. 75, 1971, 116745 z.
Chem. Abs., vol. 108, 1988, 180918 a.
Chem. Abs., vol. 103, 1985, 194381 p.
Chem. Abs. 99(5) 136790r, 1982, Hollyfield.
Chem. Abs. 107, 1987, 131994c, Williams et al.
Chem. Abs. 94, 1981, 90352j., Nippon Camphor.
Chem. Abs. 100, 1984, 114601k, Sakabe et al.
Linkewich et al, American Journal of Hospital Pharmacy, vol. 38, pp. 699–701, (May 1981).
Whitworth et al, Archives of Ophthalmology, vol. 71, pp. 493–496, (Apr. 1968).
Hackh's Chemical Dictionary, 4th ed., p. 457, 1985.

METHOD FOR TREATMENT OF GLAUCOMA WITH NITROGEN CONTAINING GUANYLATE CYCLASE ACTIVATORS

This invention was made with government support under EY05077 awarded by the National Eye Institute of the National Institutes of Health. The government has certain rights in the invention.

CROSS-REFERENCE TO RELATED APPLICATION

This application is a continuation of application Ser. No. 07/702,855, filed Nov. 21, 1990, now abandoned, which is a continuation of application Ser. No. 07/147,324, filed Jan. 22, 1988, now abandoned, which is a continuation-in-part of U.S. application Ser. No. 006,405, filed Jan. 23, 1987 now abandoned which is incorporated by reference herein in its entirety.

BACKGROUND OF THE INVENTION

1. Field of the Invention

The present invention relates to a method of treating cranial fluid volume dysfunctions including edema, hydrocephalus and glaucoma.

2. Description of the Background Art

Because the brain is encased within a rigid skull and lacks a true lymphatic drainage system, it is critically vulnerable to damage from edema. However, compared with peripheral tissues, relatively little is known about intracranial regulation of water and electrolytes. Extracellular fluid movement into and out of the brain occurs primarily at the level of the blood-brain barrier (capillary endothelium), blood-cerebrospinal fluid (CSF) barrier (choroid plexus epithelium), and CSF outflow system (dural sinus/arachnoid villae). Smith et. al., *J. Neurochem.*, 37:117 (1981); Johanson, *Encycl. Neurosci.*, (G. Adelman, Ed.) Birkhauser Boston, in press.

Pathological conditions associated with fluid accumulation in the cranium include cerebral (brain) edema and hydrocephalus, among others. Cerebral edema is a distinct and separate pathological entity from peripheral edema, and may result from a variety of causes such as stroke (including hemorrhage), anoxia, trauma, tumor, or infection. In some cases (e.g., pseudotumor cerebri or Reye's syndrome) the cause is as yet unknown.

The components of the intracranial compartment are brain, cerebrospinal fluid, and blood. Because the skull limits the total intracranial contents, the volume of the compartment is compromised with expanding lesions within the cranial cavity. The brain is virtually incompressible, so the CSF and blood serve as the main buffers of changing intracranial volume. Increases in intracranial pressure may be caused by such diverse pathologic processes as head trauma, cerebral hemorrhage, encephalitis, and brain edema. Increased intracranial pressure may not be harmful in itself, but secondary damage results either as a consequence of precipitously decreased global cerebral perfusion or herniation of brain tissue. Approximately 50% of patients who die as a result of closed head injury do so because of uncontrolled elevations in intracranial pressure.

The ability of cerebral vasculature to dilate or constrict in response to decreased or increased perfusion pressure, respectively, may also be impaired by head trauma. Occasionally, large-vessel vasospasm may also occur after acute head injury.

Intracranial tumors often cause edema of the surrounding brain tissue. Circulatory slowing and altered permeability of vessels lead to local vasogenic edema of the brain. The increased brain volume occasioned by the tumor and surrounding edema may raise the pressure in one of the cranial compartments to the point that the brain tissue is displaced into an adjacent compartment. In this way brain herniations occur. Regional edema causes a rapidly evolving impairment of the function of the part of the brain involved.

Pathologic intracranial infections may also lead to intracranial edema. The early reaction to bacterial invasion of the brain includes localized inflammatory necrosis and edema. Persistence or progression of high intracranial pressure may cause deepening coma and threat of herniation.

Hydrocephalus is a condition of increased intracranial pressure caused by obstruction to the movement or impairment of the reabsorption of cerebrospinal fluid (CSF). This can result from congenital defects, infections, cerebral hemorrhage, inflammatory conditions, and other conditions. Cerebrospinal fluid is normally secreted by the choroid plexus, a tissue located in the cerebral ventricles.

Glaucoma is a condition of the eye associated with high pressure due to an impediment in the outflow of the aqueous fluid (aqueous humor), which is normally secreted by the ciliary process (a tissue similar in function to the choroid plexus). In 90% of cases the cause is unknown, while in 5%, the condition is secondary to some disease process that blocks the outflow channels. Glaucoma occurs in 2% of all patients over 40; it may be asymptomatic and unrecognized before it progresses to rapid vision loss. The normal pressure is about 15 mmHg. Pressures of 20–30 mmHg may damage the optic nerve and lead to blindness.

Prior to the present invention, methods of treating cerebral edema have included administration of urea, mannitol, or cortisone derivatives. These treatments are often inadequate and patients can go on to develop severe neurological sequelae or even death. Even surgical fluid drainage (ventriculostomy) often can not prevent these sequelae. Pharmacological treatment of hydrocephalus has also been quite disappointing. Patients often require a permanent surgical shunt, a procedure which has serious side effects, including infection and subdural hematoma. In the area of glaucoma, some advances have been made with the introduction of beta-adrenergic blockers. However, these agents can have serious pulmonary and cardiovascular side effects, including asthma and congestive heart failure.

Recently, it has been suggested that a group of peptides, released from atrial cardiac myocytes, are key hormones for regulating fluid volume in the periphery. Cantin and Genest, *Endocrine Rev.*, 6:107 (1985); deBold, *Science*, 230: 767 (1985). These peptides are known as atrial natriuretic peptides, atrial natriuretic factors (ANF), or atriopeptins (ANP), and have been isolated from a variety of species, including man. In response to fluid overload, atriopeptins are released into the circulation and cause rapid diuresis and natriuresis through both direct and indirect effects on the kidney. Atriopeptins are also known to induce systemic vasodilation through an endothelial-independent mechanism. Windquist, *Life Sci.*, 37:1081 (1985). Reports of studies in peripheral tissue suggest that the atriopeptin receptor occupancy is associated with the intracellular production of guanosine 3',5'-monophosphate (cyclic GMP). Waldman et. al., *J. Biol. Chem.*, 259:14332 (1984); Winquist et. al., *Proc. Natl. Acad. Sci. USA*, 81: 7661 (1984). Atriopeptin receptors have been identified by autoradiographic studies in kidney and (peripheral) vasculature as well as in other tissues including brain (hypothalamus and circumventricular organs), pituitary, intestine, adrenal, and ciliary body. Napier et al., *Proc. Natl. Acad. Sci. (USA)*, 81:5946 (1984); Gibson et al., *J. Neurosci.*, 6:2004 (1986).

Many hormones act through "second messengers" such as cyclic AMP (cAMP) or cyclic GMP (cGMP). An accepted model of hormone action involves the binding of a hormone to a hormone-specific cell membrane-bound receptor which activates a hormone-sensitive adenylate (for cAMP) or guanylate (for cGMP) cyclase to a form capable of converting ATP (or GTP) in the cytoplasm of the cell into cAMP (or cGMP). The cAMP (or cGMP) then relays the signal brought by the hormone from the membrane to the interior of the cell. Agonists of the hormone are, by definition, capable of eliciting the same response (see, for example, Nathanson and Greengard, *Scientific American*, 237:108–119 (1977) for a discussion involving cyclic nucleotides).

Once formed inside cells, cAMP and cGMP are broken down by a group of enzymes called cyclic nucleotide phosphodiesterases (hereafter called phosphodiesterase). Pharmacological inhibition of phosphodiesterase results in prolonged and augmented levels of cAMP and cGMP within cells, and can cause physiological responses similar to those of the original hormone.

SUMMARY OF THE INVENTION

The present invention arose out of the observations by the inventor that blood-brain barrier tissues are end organs for atriopeptins and that atriopeptin receptors in the secretory epithelial cells of the choroid plexus of the brain and the ciliary process of the eye are coupled to the activation of guanylate cyclase activity. Based upon these observations, the inventor hypothesized that compounds which are interactive with the atriopeptin receptors, or other nitrogen-containing guanylate cyclase activators, or compounds which are phosphodiesterase inhibitors, might be useful in the treatment of glaucoma and various conditions associated with pathological intracranial fluid accumulation. Investigation of this hypothesis has led to the present invention which relates to the treatment of fluid volume dysfunctions in the brain and eye (cranial fluid volume dysfunction) with at least one compound selected from atriopeptins, their analogues and agonists, other nitrogen-containing guanylate cyclase activators, and those agents which are inhibitors of phosphodiesterase enzymes (those enzymes which are capable of hydrolyzing cGMP).

Thus, in one embodiment, the present invention provides a method of treating fluid volume dysfunction of the cranium in an individual in need of such treatment which comprises administering a fluid volume decreasing amount of an atriopeptin, an analogue or agonist thereof, other nitrogen-containing guanylate cyclase activators, or an agent capable of inhibiting a phosphodiesterase enzyme which degrades cGMP to said individual.

In addition to drugs which act directly on atriopeptin receptors, the inventor has developed additional pharmacological strategies which involve manipulation of the intracellular second messenger system (cyclic GMP) involved in atriopeptin action. Drugs acting on cyclic GMP (cGMP) have physiological effects similar to those of the atriopeptins. In addition, such drugs can be designed to be well absorbed through the oral or topical routes of administration. This considerably broadens the scope of the approach to treating cranial volume dysfunctions which involve a number of different types of chemical compounds, including for example, nitroglycerine, sodium nitrite, hydralazine, and minoxidil. This group of nitrogen-containing guanylate cyclase activating agents includes the nitro compounds, which stimulate cyclic GMP formation in brain and eye secretory tissues. When administered topically, i.e., as eye drops, at very low concentrations, these guanylate cyclase activators, nitroglycerine, for example, cause a substantial decrease in intraocular pressure without observable side effects on the eye. In addition, the topical administration decreases IOP without decreasing systolic, diastolic, or mean systemic blood pressure and without affecting cardiac pulse rate.

These agents may be synergistic, i.e., the administration in combination of an atriopeptin or atriopeptin agonist and a phosphodiesterase inhibitor or another nitrogen-containing guanylate cyclase activator and atriopeptin, for example, may result in the correlated action of both compounds which, together, have greater total effect than the sum of their individual effects.

BRIEF aDESCRIPTION OF THE DRAWINGS

FIGS. 1A, 1B and 1C demonstrate the effect of rat atrial natriuretic peptide 1–28 (rANP) on membrane bound guanylate cyclase (FIG. 1A and FIG. 1B) and adenylate cyclase (FIG. 1C) activity in various brain barrier tissues and tissue fractions from rabbit compared with activity in cerebrum and cerebellum.

Figure 4:
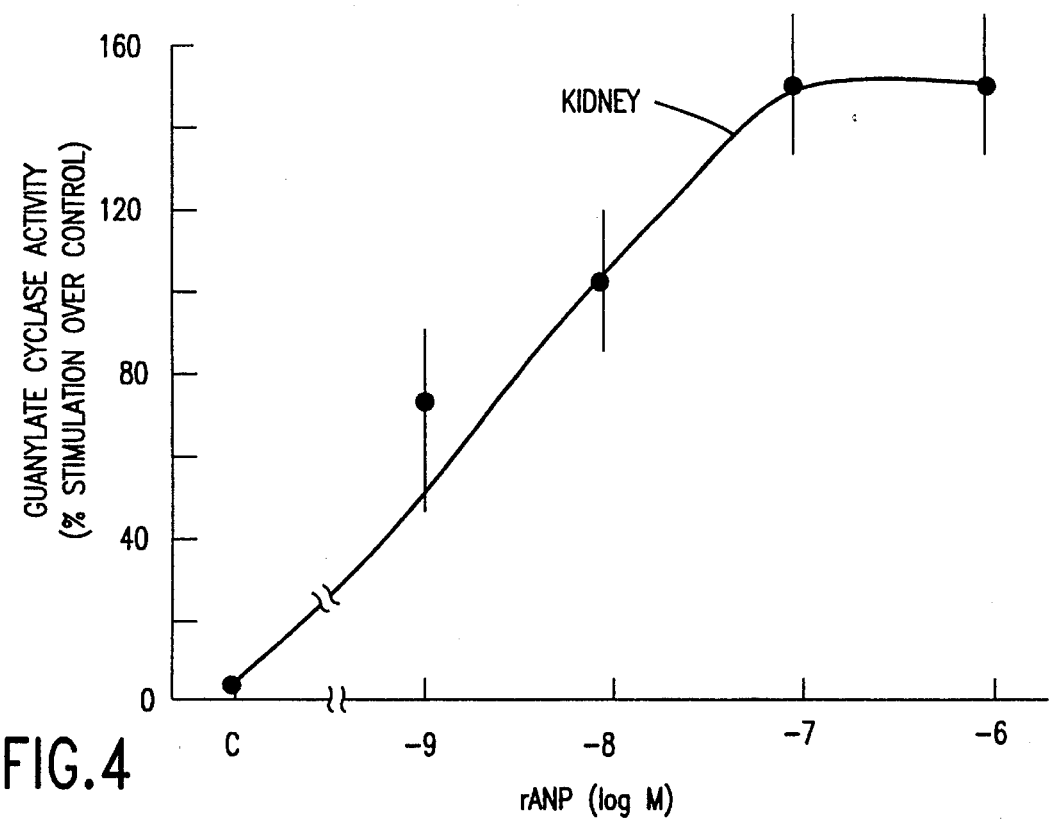

FIG. 4 demonstrates atriopeptin-activated guanylate cyclase activity in membrane preparations from rabbit kidney. Values shown are the means±range for duplicate guanylate cyclase determinations, each assayed by radioimmunoassay (RIA) in triplicate. Control activity was 7.1 pmol/mg protein/min.

Figure 5:
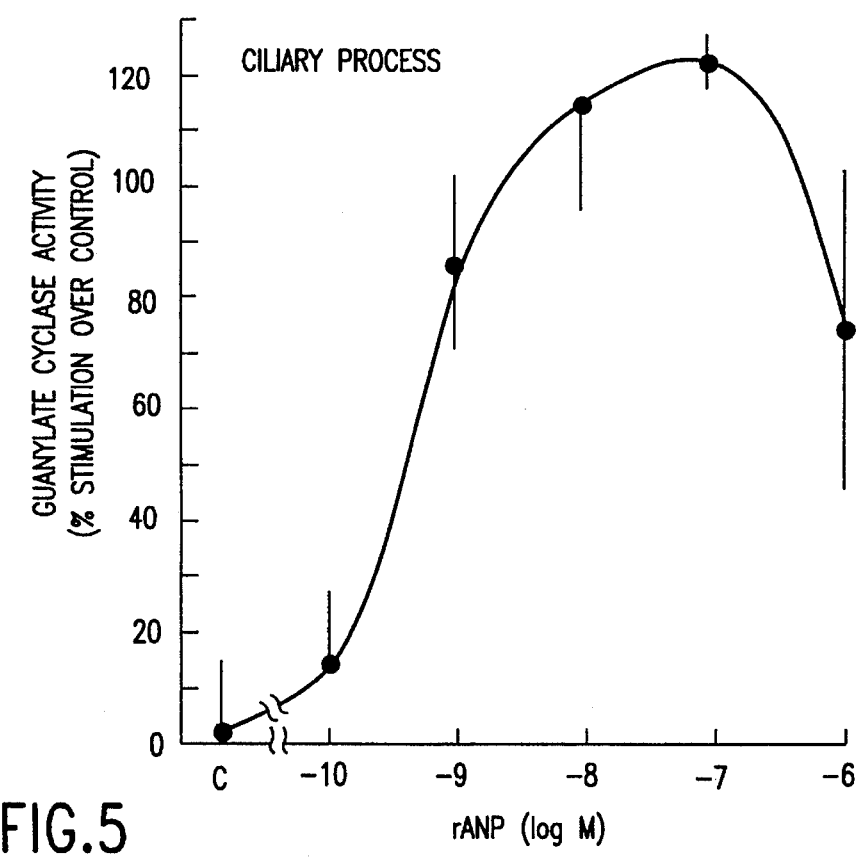

FIG. 5 demonstrates atriopeptin-activated guanylate cyclase activity in membrane preparations from isolated rabbit ciliary processes. Values shown are the means±range for duplicate guanylate cyclase determinations, each assayed by radioimmunoassay (RIA) in triplicate. Control activity was 75±10 pmol/mg protein/min.

Figure 6:
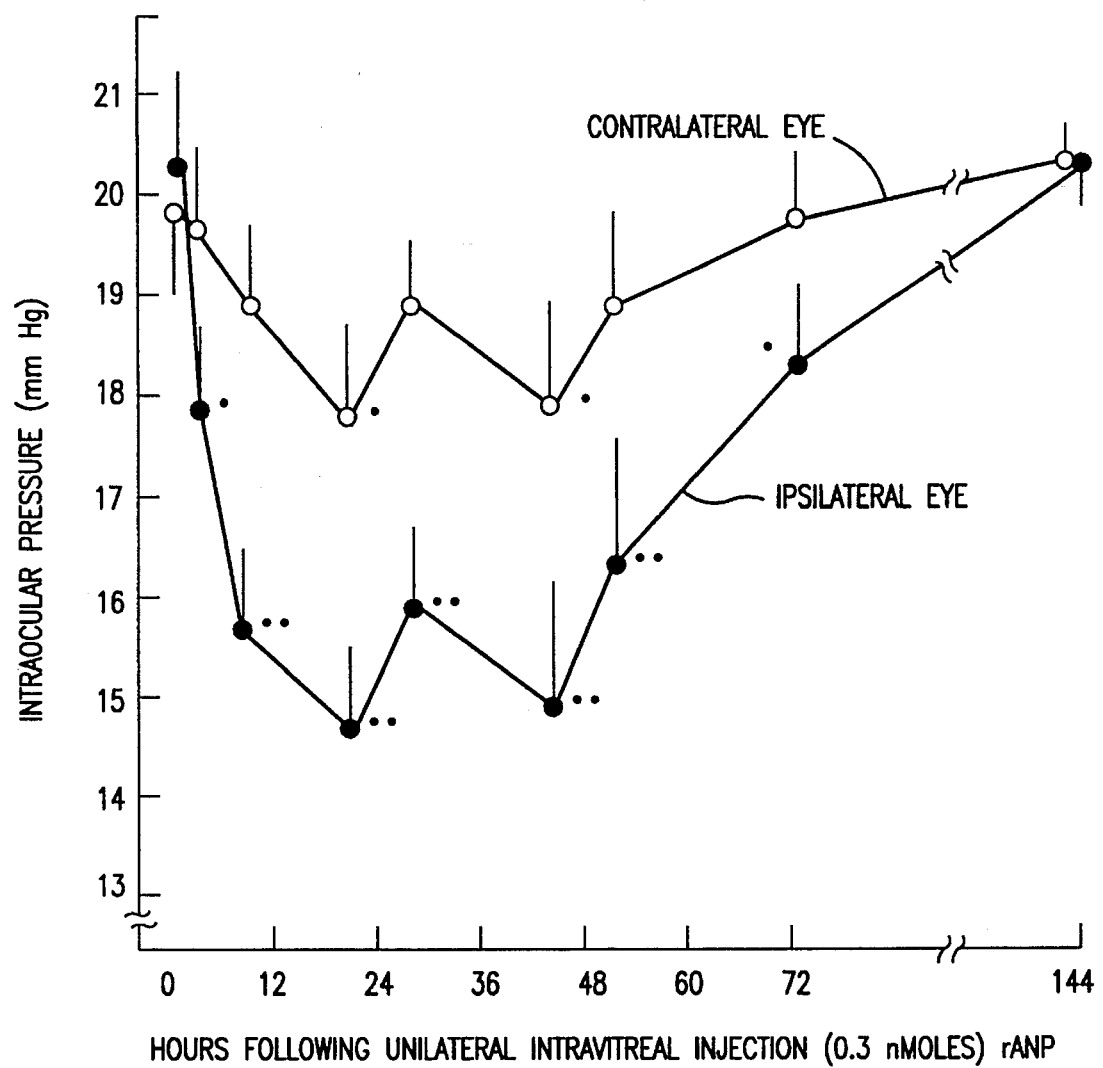

FIG. 6 demonstrates the effect of unilateral intravitreal injection of 0.3 nmoles of rANP 1–28 on intraocular pressure in a group of eight albino rabbits. The contralateral eye received intravitreal injection of vehicle alone. Filled circles represent the IOP in ipsilateral eye; open circles represents the IOP in contralateral eye.

Figure 7:
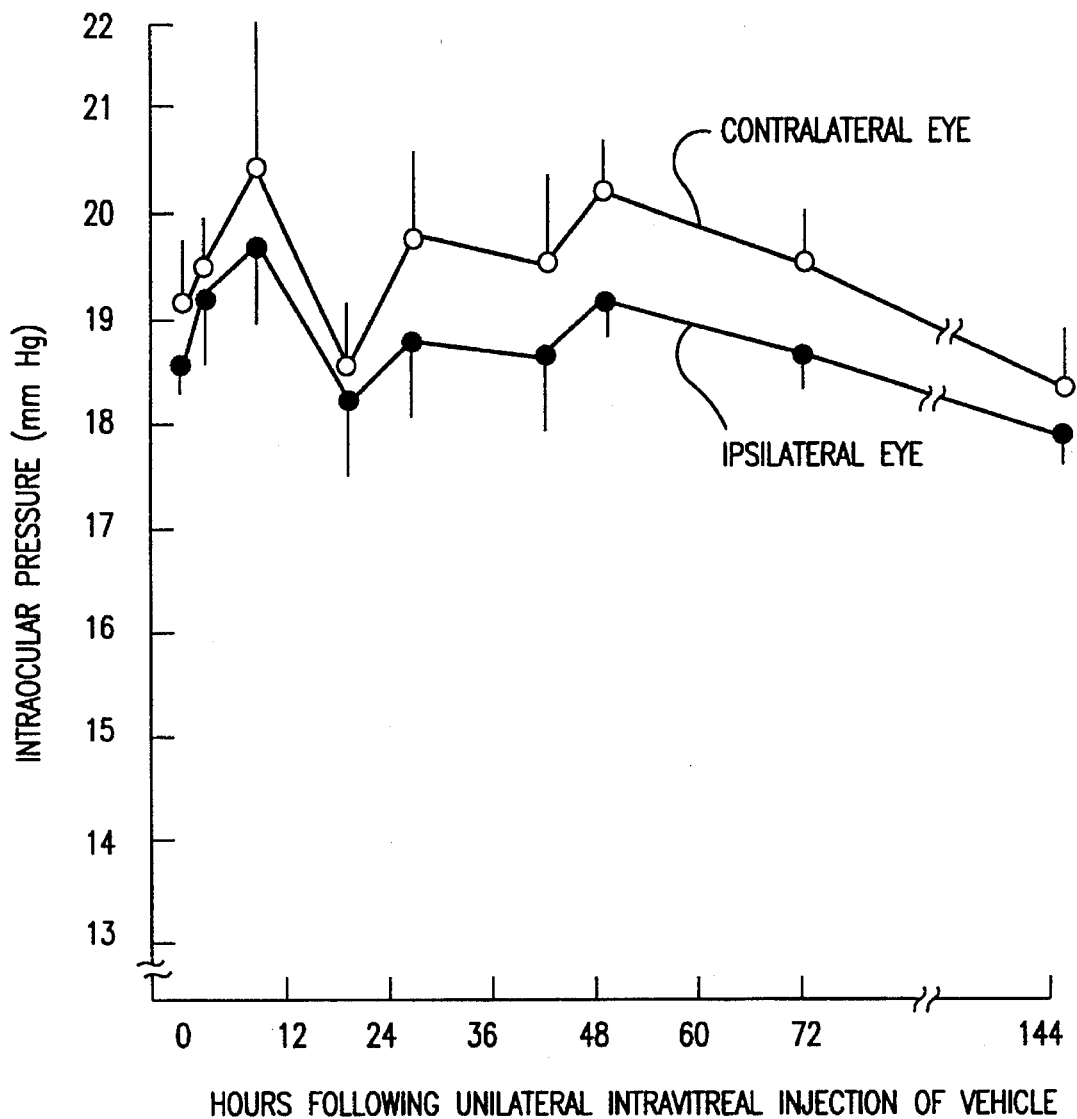

FIG. 7 demonstrates the effect of unilateral intravitreal injection of vehicle (artificial aqueous humor) on IOP in a group of five albino rabbits. Contralateral eyes received nothing. There were no statistically significant differences between ipsilateral and contralateral IOP and no significant changes in IOP following injection.

Figure 8:
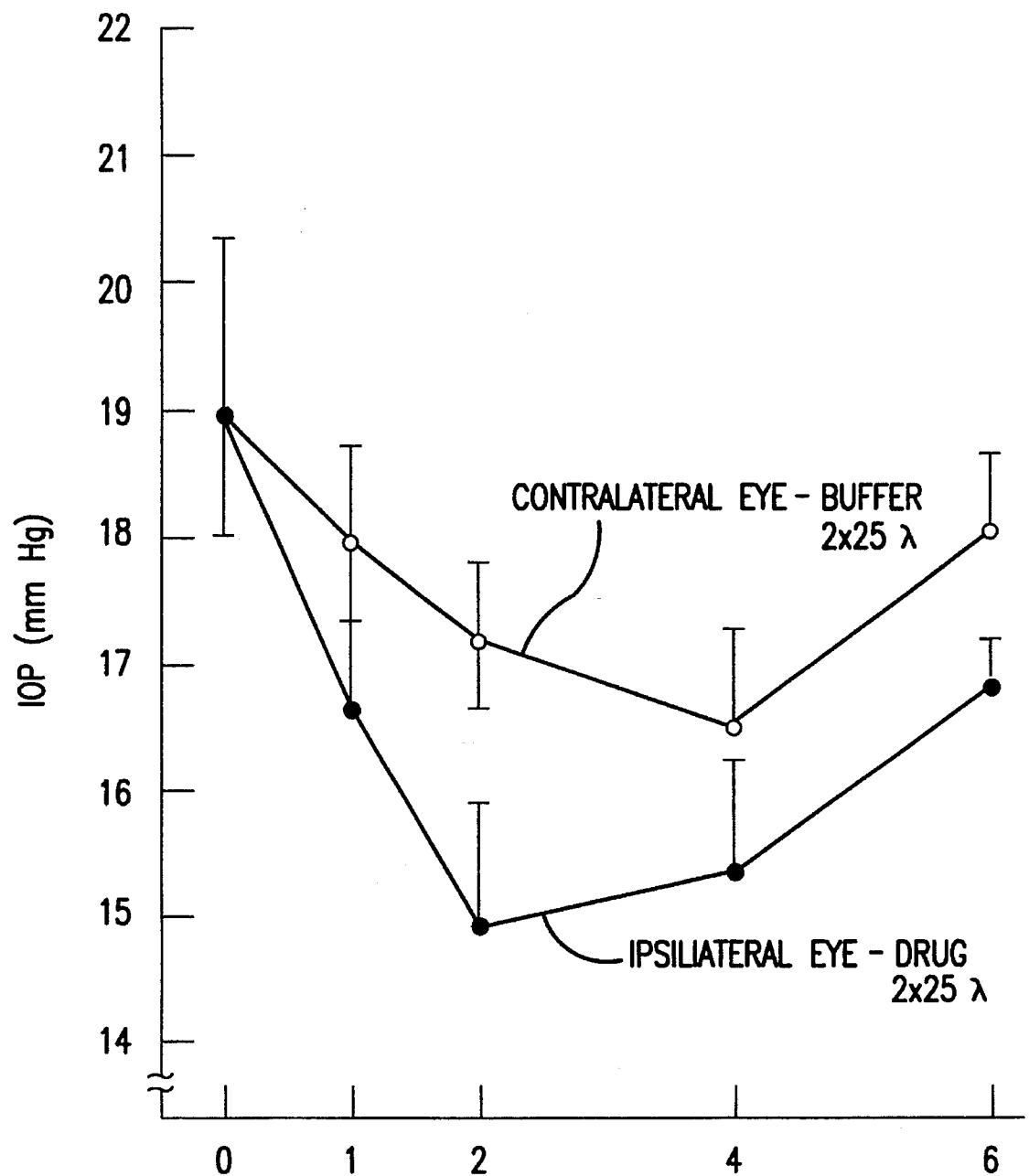

FIG. 8 demonstrates that topical application of inhibitors of PDE cause a decrease in intraocular pressure in the rabbit eye.

A potent PDE inhibitor of the arylxanthine class, 1,3-dibutyl-xanthine, was applied unilaterally and topically to rabbit eyes in a 0.5% solution. There was a small decrease in the IOP in the contralateral eye, possibly due to systemic absorption. The IOP was decreased 4 mm (Hg) in the ipsilateral eye.

Figure 9A:
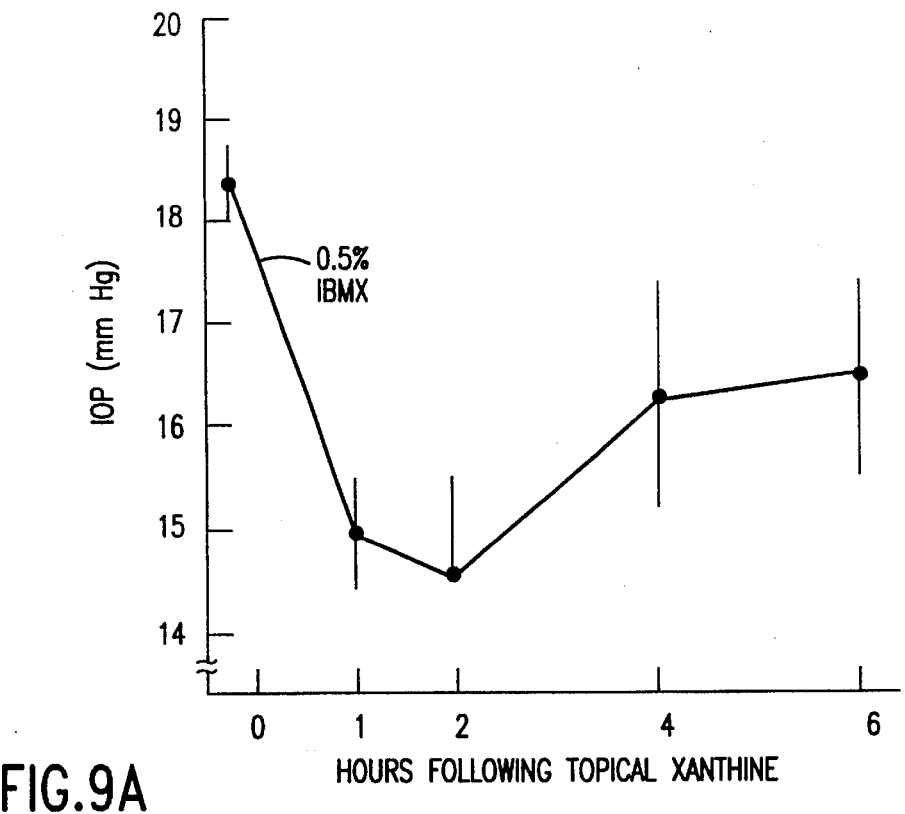
Figure 9B:
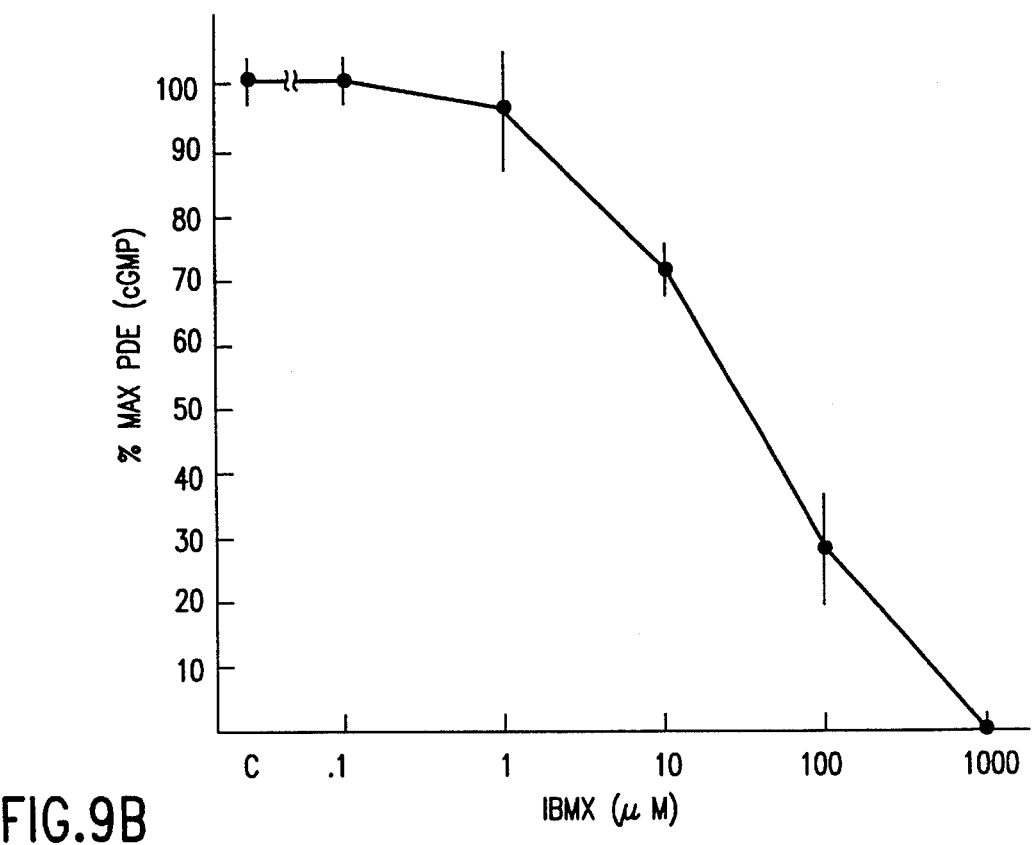

FIGS. 9A and 9B demonstrate the effect of 1-methyl-3-isobutyl-xanthine on IOP and PDE inhibition in ciliary process.

Figure 10:
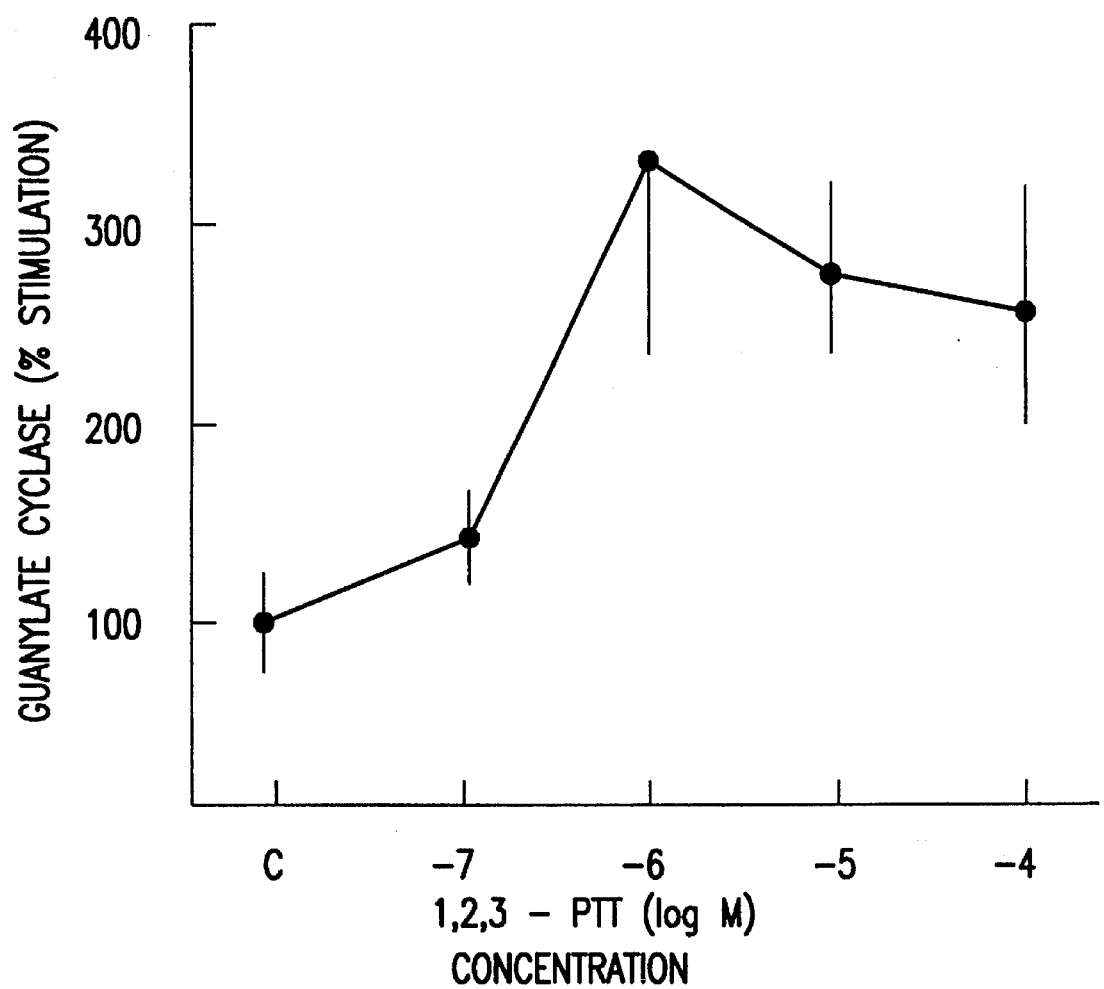

FIG. 10 demonstrates the effect of 1,2,3-propanetriol trinitrate (nitroglycerine) on the activation of guanylate cyclase in the ciliary process of the rabbit.

Figure 11:
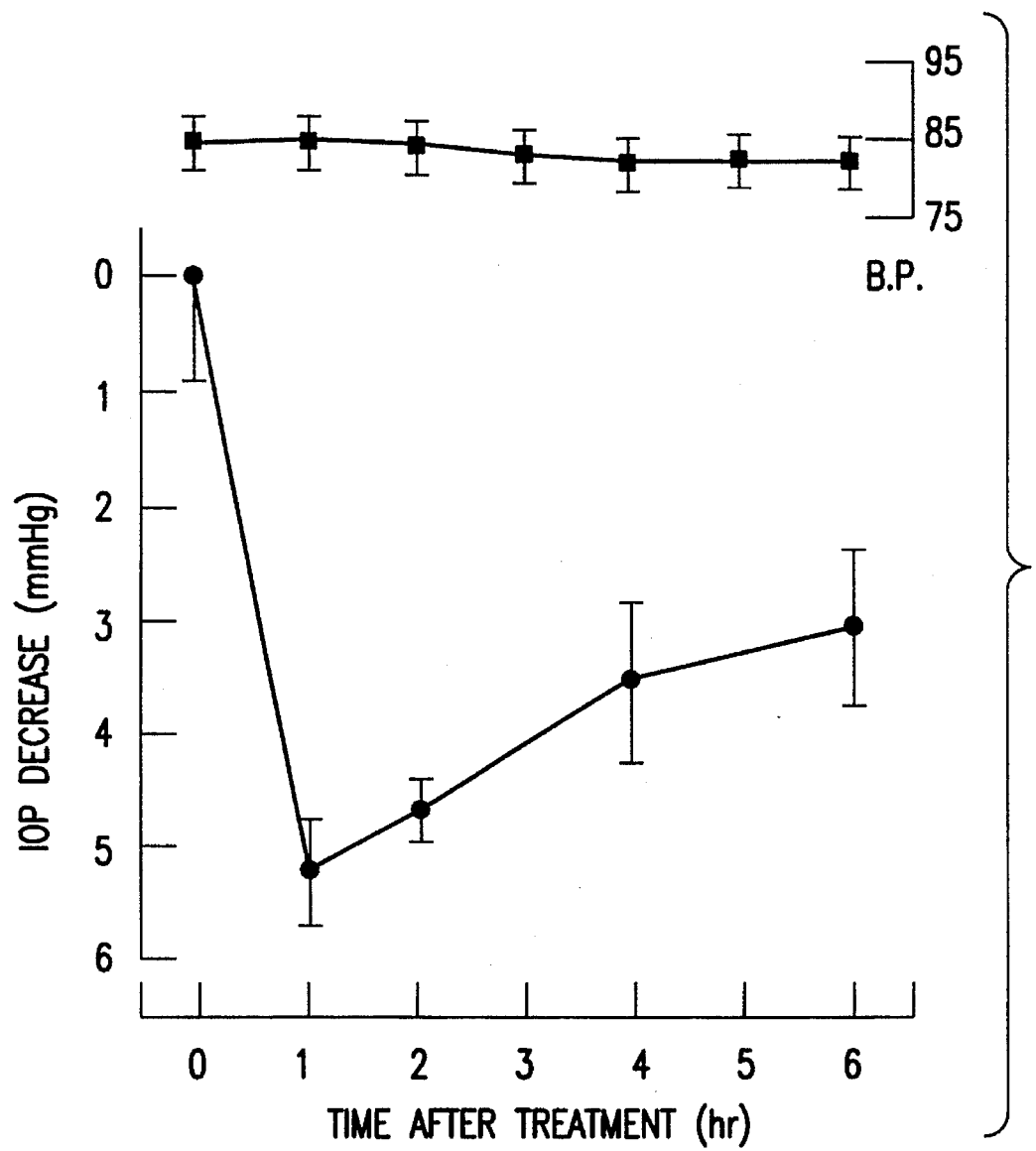

FIG. 11 demonstrates the effect of the administration of nitroglycerine as an eye drop preparation on the IOP in rabbits. The decrease in IOP is not accompanied by a concommitant decrease in systemic blood pressure.

Figure 12:
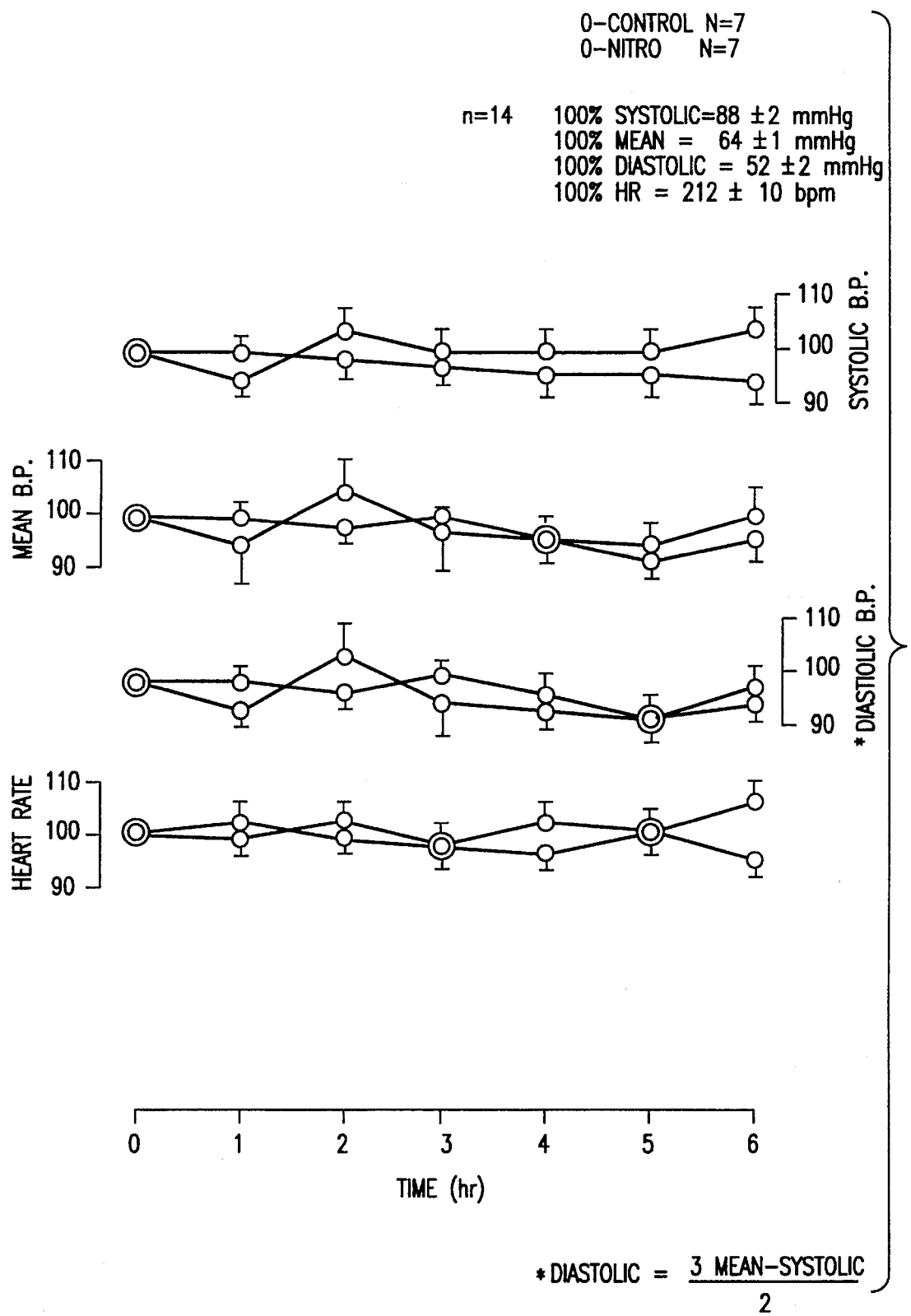

FIG. 12 additionally shows the absence of effect on pulse rate or systemic blood pressure from the administration of an eye drop preparation of nitroglycerine in rabbits.

Figure 13:
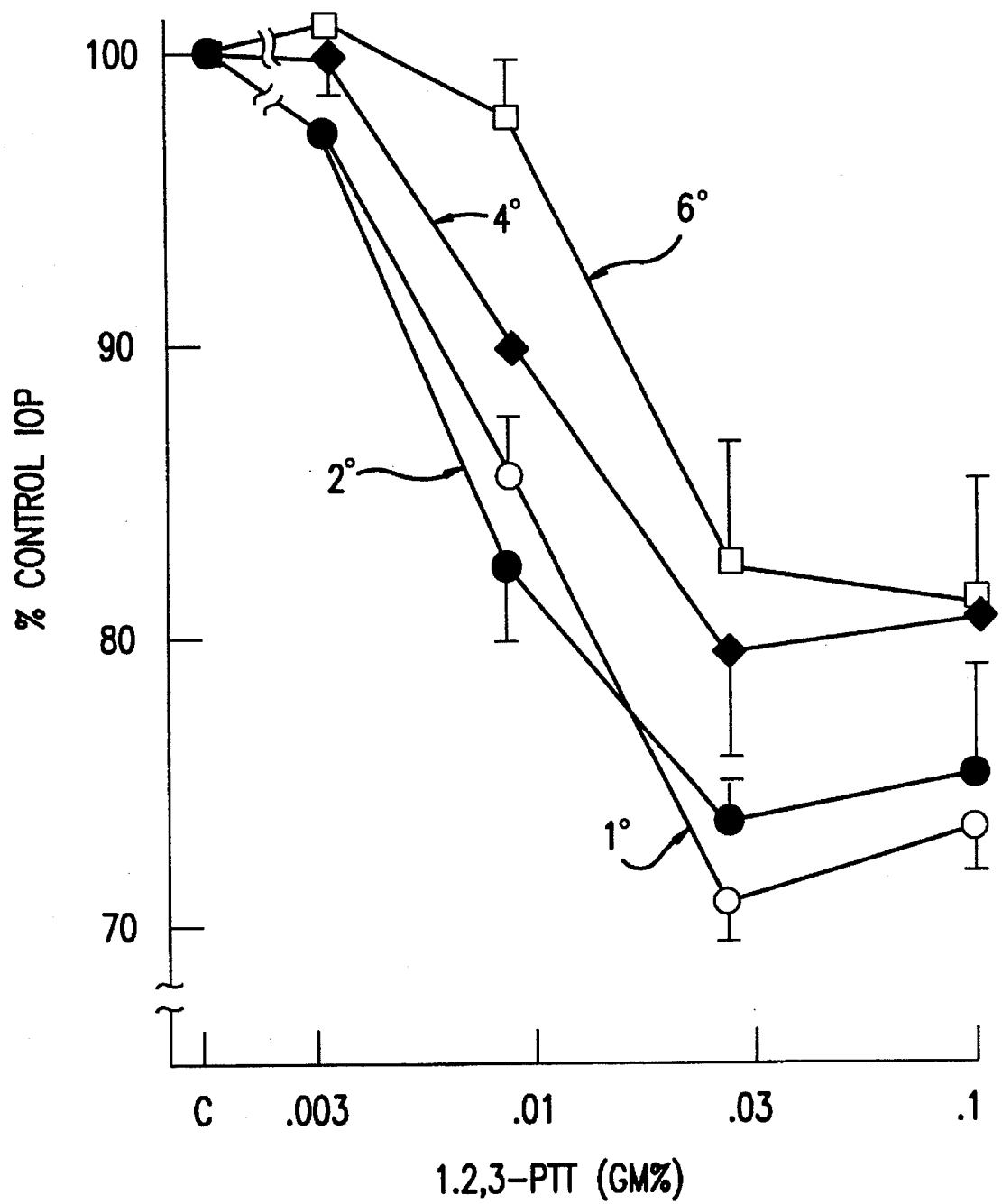

FIG. 13 illustrates that doses of nitroglycerine eye drops (50 μl of 0.1% aqueous solution) caused no additional decrease in IOP and that lower doses were less effective.

Figure 14:
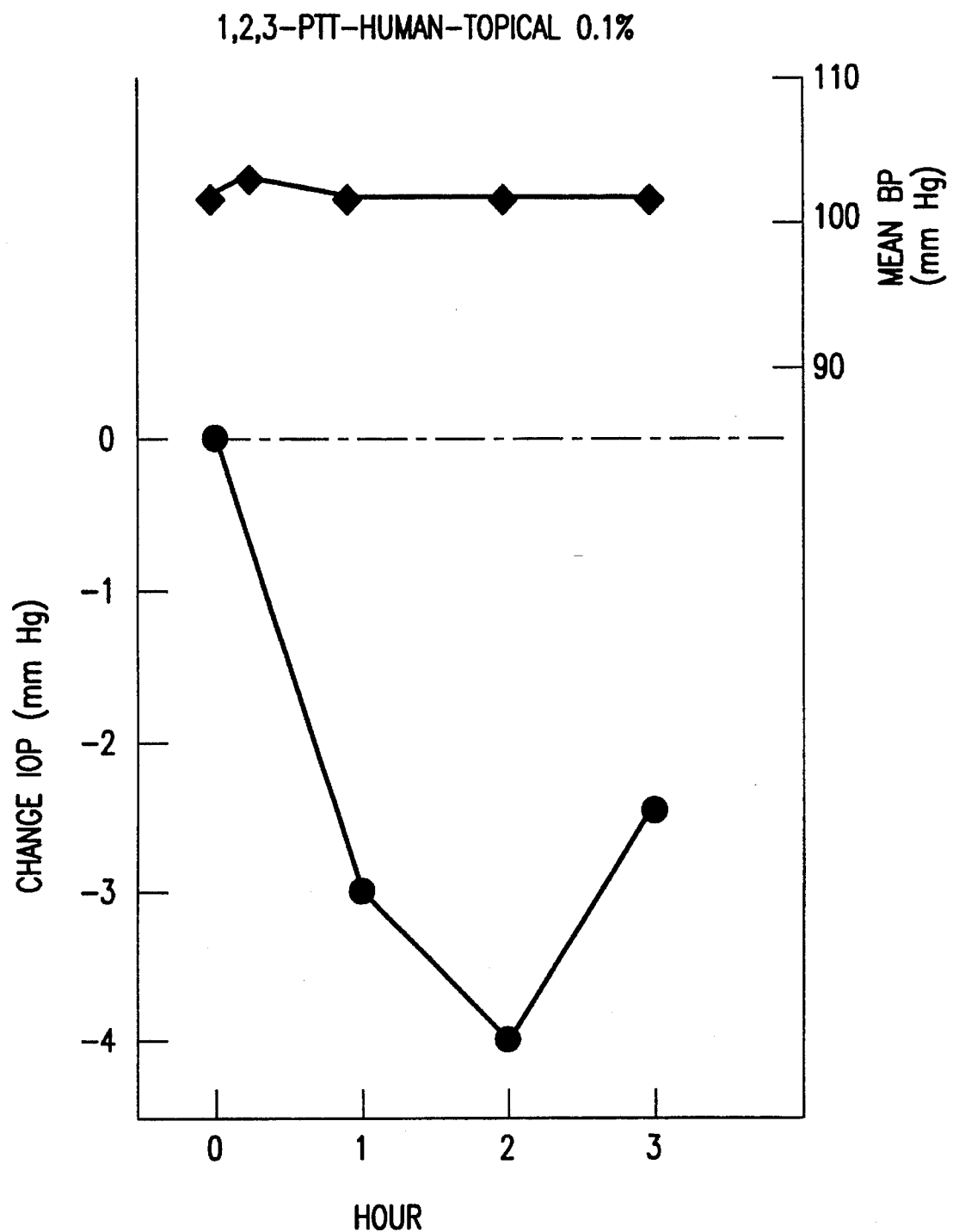

FIG. 14 illustrates the effect of the administration of a nitroglycerine eye drop preparation (50 μl of 0.1% aqueous solution in one eye) in a volunteer human. Importantly, although the nitroglycerine eye drops decreased IOP, they did not affect systemic blood pressure.

Figure 15:
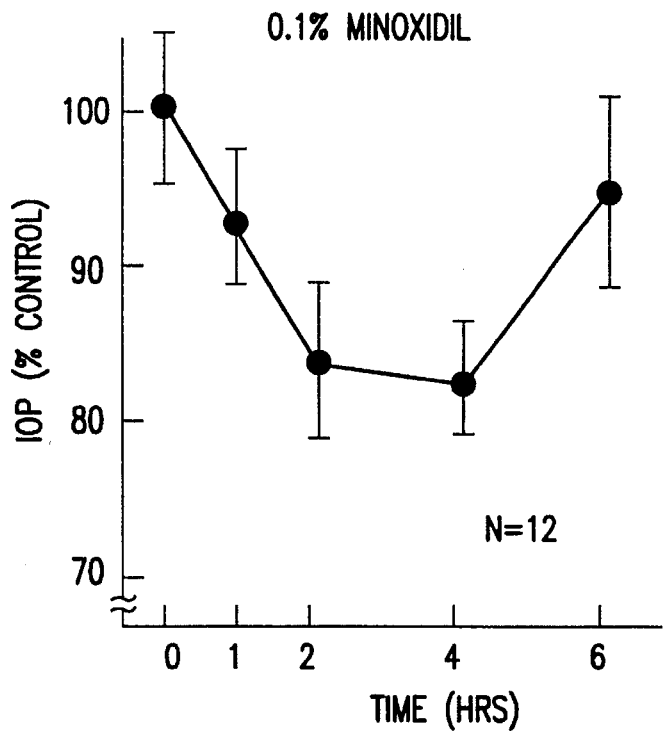

FIG. 15 demonstrates that a 50 μl 0.1% aqueous eye drop solution of minoxidil, a nitrogen-containing guanylate cyclase activator, decreases the IOP in rabbits.

Figure 16:
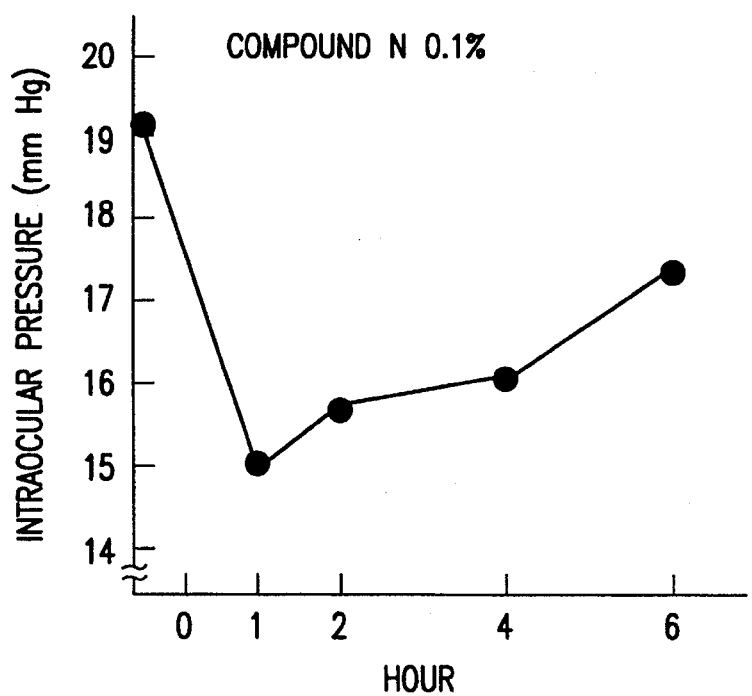

FIG. 16 illustrates that a 50 μl 0.1% aqueous eye drop solution of sodium nitrate, another nitrogen-containing guanylate cyclase activator, lowers the IOP in rabbits.

Figure 17:
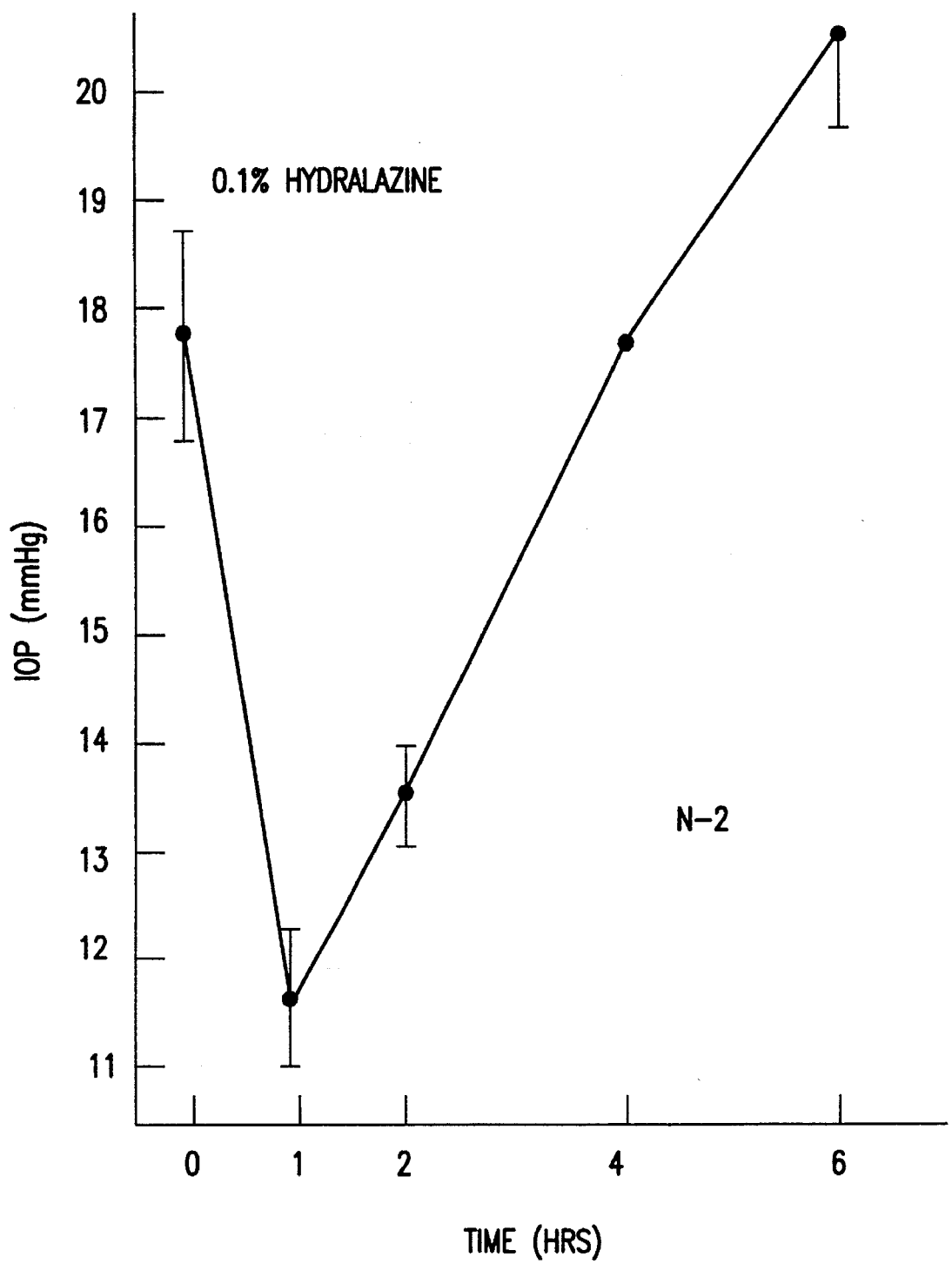

FIG. 17 demonstrates that a 0.1% eye drop preparation of hydralazine decreases the IOP in rabbits.

DESCRIPTION OF THE PREFERRED EMBODIMENTS

The method of the present invention is useful for treatment of cranial fluid volume dysfunction of any origin in an individual. By the term "cranial fluid volume dysfunction" is intended those pathological conditions associated with an overproduction or decreased rate of removal of fluid from the cranium including the eye.

Typical cranial fluid volume dysfunctions include, but are not limited to, brain edema, hydrocephalus, and glaucoma.

The term "individual" is intended to include any animal, preferably a mammal, and most preferably, a human.

Compounds useful in the practice of the present invention include those compounds which act directly on the atriopeptin receptors of the brain (including membranes, blood vessels, choroid plexus and CSF reabsorptive areas), spinal cord, and ciliary process and trabecular meshwork of the eye to activate guanylate cyclase (hereinafter atriopeptin-sensitive guanylate cyclase activators) and further include those compounds which act through the mechanism of inhibition of phosphodiesterase activity relating to degradation of cGMP.

The compounds useful in the present invention which act directly upon the atriopeptin receptor sites to activate guanylate cyclase include, but are not limited to, atriopeptins, atriopeptin analogues, and atriopeptin agonists. In addition, nitrogen-containing guanylate cyclase activators have been discovered to be useful in the present invention.

The term atriopeptin is meant to include atrial natriuretic factors and their precursor polypeptides, as well as peptides having atriopeptin activity, regardless of the source. Atriopeptin precursors are polypeptides which include an atriopeptin amino acid sequence within a longer sequence of amino acids which precursors may or may not exhibit atriopeptin activity in vitro. Typical atriopeptins include naturally occurring as well as synthetic atriopeptins and active fragments thereof. Among the atrial natriuretic factors which may be used in the present invention are peptides or their precursors, with amino acid sequences such as the following naturally occurring sequences isolated from the human and rat, respectively:

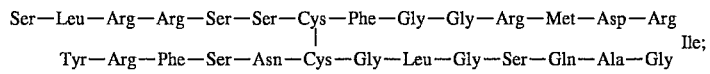

and

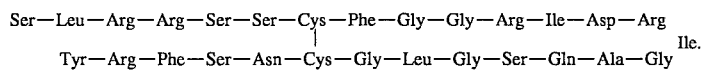

Also active are sequences identical to those above but lacking the N-terminal Ser, the N-terminal Ser-Leu, the N-terminal Ser-Leu-Arg, the N-terminal Ser-Leu-Arg-Arg, or the C-term Tyr. Also active are longer sequences such as those above additionally consisting of Arg-Pro-Gly-Ala at the N-terminal end.

Typical analogues of atriopeptin useful in the present invention include, but are not limited to peptides which may mimic the naturally occurring atriopeptins or vary by one or more amino acids and which demonstrate biological activity substantially similar to that of atriopeptins, such as

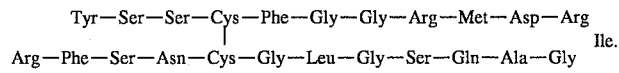

Typical atriopeptin agonists are compounds which demonstrate biological activity substantially similar to that of atriopeptins. Such atriopeptin agonists include compounds which bind to the atriopeptin receptor as well as compounds which activate the atriopeptin-sensitive guanylate cyclase. Typical atriopeptin agonists would include, but are not limited to, compounds such as nonpeptide analogues interacting with the receptor, and nitro compounds such as sodium azide, sodium nitrite, or nitroglycerine, which directly interact with guanylate cyclase.

In addition, nitrogen-containing guanylate cyclase activators, including inorganic nitrites like sodium nitrite, organic nitrates such as nitroglycerine and pentaerythritol tetranitrate, and non-nitrate nitrogen-containing compounds such as hydralazine and minoxidil are also useful in the present invention.

A suitable screening method for determining whether a given compound is an atriopeptin agonist or analogue comprises measuring guanylate cyclase activity of the atriopeptin-sensitive guanylate cyclase in broken cell preparations of choroid plexus (or epithelial cells) by a modification of the technique of Waldman et. al. Said modified technique is described in detail in Example 1.

Generally, the broken cell preparations are prepared according to the method described in a paper by Nathanson et al., *Molecular Pharmacology* 20:68 (1981), which is herein incorporated by reference. Choroid epithelial cells are prepared as described in Example 1. To measure activity of atriopeptins, analogues, or agonists thereof, washed particulate cell preparations are prepared by using the pellet obtained following high speed centrifugation. To measure direct activators of guanylate cyclase, the crude broken-cell preparation without centrifugation is used. Guanylate cyclase activity is measured in appropriate buffer-containing GTP, cofactors, tissue fraction, and the compound to be tested. If necessary, the compounds to be tested are initially solubilized and appropriate solvent controls are run in parallel. The enzyme reaction is initiated by addition of GTP, stopped by heating, and centrifuged. Cyclic GMP can be measured by any test which indicates the presence thereof, typically by the radioimmunoassay as described in Example 6. Normally, the solution mixture contains a phosphodiesterase inhibitor such as theophylline, so as to provide linear measurements with respect to time and enzyme concentration. The determination of the constant $K_a$, which is the concentration of agonist necessary for half-maximal activation of cyclase activity, is carried out by measuring cyclase activity in the preparation, and plotting the activity (above control activity) versus the semilogarithm of the particular agonist concentration. This is done for a series of increasing concentrations until maximal activity ($V_{max}$) is reached. $K_a^B$, where B is the test compound, is compared with the constant ($K_a^{ANF}$) determined in an analogous way using rat atrial natriuretic factor (rANF) as a standard. The ratio $K_a^{ANF}/K_a^B$ is then an indication of whether the compound (B) is better (ratio greater than 1) or worse (ratio smaller than 1) than rANF. Maximal activation of enzyme activity as a percentage of maximal activation seen in the presence of rANF can be denoted as % $V_{max}$.

Typical compounds capable of inhibiting a phosphodiesterase enzyme useful in the method of the present invention include those compounds which prevent or greatly decrease the hydrolysis of endogenous cGMP produced by activation of guanylate cyclase. The inhibition of cGMP phosphodiesterase may be either through a competitive or non-competitive mode. Further, the cGMP phosphodiesterase inhibited should be that found in the particular cranial tissue of the species being treated. Thus, the testing of any particular PDE inhibitor can be carried out on PDE isolated from or found in choroid plexus (or epithelial cells) or ciliary process.

The ability of any compound to inhibit cGMP phosphodiesterase (PDE) activity in broken-cell preparations of choroid epithelial cells or ciliary process can be determined either 1) by measuring the decrease in rate of hydrolysis of an added amount of cyclic GMP by PDE (see, Methods Section of Nathanson et al., *Mol. Pharmacol.* 12:390–398 (1975)), or 2) by measuring the rate of accumulation of one of the breakdown products of cyclic GMP, such as 5'-GMP or guanosine (see method of Filburn et al., *Anal. Biochem.* 52:505–516 (1973)). Both of these are herein incorporated by reference.

Generally, any compound capable of maximally inhibiting PDE activity by at least 50% ($V_{max}$-inhibition) and preferably by at least 80% is preferred. Also, in terms of the concentration of the compound required for such inhibition, this can be quantitated by determining the $IC_{50}$-inhibition, i.e., the concentration of the compound required to cause 50% of the maximal inhibition caused by the compound at any concentration. Generally, any compound with an $IC_{50}$-inhibition for PDE of less than 10 mM and preferably less than 2.5 mM is preferred.

Of particular interest are purine derivatives, such as theophylline, xanthine, methylxanthine, isobutylmethylxanthine (IBMX), and lower alkyl or substitution homologues or analogues thereof. See, e.g. Kramer, et al., *Biochem.*, 16:3316 (1977); Garst et al,, *J. Med. Chem.*, 19:499 (1976); Amer et al., *J. Pharm. Sci.*, 64:1 (1975); or Beavo etal., *Mol, Pharm.*, 6:597 (1970). For the purposes of this invention, halide, hydroxy, keto, lower alkoxy, lower straight alkyl, lower branched alkyl, amino, lower alkylamino, lower halo alkyl, fluorine, chlorine, bromine, iodo, azido, nitro, mercapto, alkene-oxy, cyano, alkyl-cyano, phenyl, benzyl, substituted benzyl, or the like substituents on any of the aforementioned compounds are equivalent if they do not substantially block the agonistic activity of the atriopeptinergic agonist.

Of interest are also the phosphodiesterase inhibitors described by Rojakovick e. al., (*Pesticide Biochemistry and Physiology*, 610–19 (1976)) which belong to the family of quinoxaline dithiols. These compounds, denoted as oxythioquinox, SAS 2185, 1948, 2501, 2061, 2551 or 2079, are those of the formula:

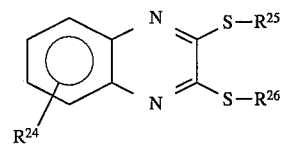

where $R^{24}$ can be hydrogen, lower alkyl, lower alkoxy or trifluoromethyl, $R^{25}$ and $R^{26}$ can be the same or different and selected from the group of H, $COOR^{27}$, where $R^{27}$ is lower alkyl; or both $R^{25}$ and $R^{26}$ taken together may form a group of the formula —CO—, bridging both S atoms.

Another family of PDE inhibitors are the benzylisoquinoline derivatives, such as papaverine (See, for example, U.S. Pat. No. 3,978,213 to Lapinet et al., which relates to the cosmetic use of mixtures of cyclic AMP and phosphodiesterase inhibitors; or Amer et al., supra).

Another family of PDE inhibitors are the substituted pyrrolidones, such as 4-(3-cyclopentyloxy-4-methylphenyl)-2-pyrrolidine (ZK62711). See Schwabe et al., *Mol. Pharmacol.* 12:900–910 (1976).

Another family of PDE inhibitors are the 4-(3,4-dialkoxybenzyl)-2-imidazolidinones, such as (4-(3-butoxy-4-methoxbenzyl)-2-imidazolidinone (Ro 20-1724). See Sheppard et al., *Biochem. J.* 120:20P (1970).

Another family of PDE inhibitors are the benzodiazepine derivatives, such as diazepam. See Dalton et al., *Proc. Soc. Exp. Bio. Med.* 145:407-10 (1974).

Another family of PDE inhibitors are the tricyclic agents, such as the phenothiazines. See Honda et al., *Biochem. Biophys. Acta* 161:267 (1968).

Another family are various purine-ribose derivatives, including puromycin and derivatives of cyclic nucleotides (other than cyclic AMP or active cyclic AMP analogues). See Amer et al., *J. Pharm. Sci.* 64:1–37 (1975) Table VI.

Another PDE inhibitor is SQ20009: (1-ethyl-4-isopropylidene-hydrazino-14-pyrazolo(3,4)pyridine-5-carboxylate ethyl ester.) See Beer et al., *Science* 176:428 (1972).

Other PDE inhibitors include M&B22948, dilazep, MY5445 and OPC3689. See, Hidaka et al., TIPS, pp 237–239 (June 1984) and Bergstrand et al., *Molec. Pharmacol.*, 13:38–43 (1977).

In general, any compound which inhibits PDE as described above and which, at the same concentration, does not substantially block the activity of the guanylate cyclase activator or atriopeptin agonist in stimulating guanylate cyclase or atriopeptin-sensitive guanylate cyclase (as measured above) and is non-toxic to the individual to be treated, can be used.

The PDE inhibitor may be present alone or in combination with other active or non-active compounds.

The molecular inhibition of PDE in vitro by a PDE inhibitor correlates with the molecular inhibition of the enzyme in vivo. However, it may be that a compound which is an excellent PDE inhibitor in vitro does not show good in vivo activity. Other factors, such as possible metabolism, transport or absorption of the compound may influence its overall effectiveness. One of skill in the art, however, can by a simple preliminary trial measuring intracranial pressure or intraocular pressure, ascertain quite quickly and routinely whether a chosen agent is useful in vivo.

Administration of the compounds useful in the method of the present invention may be by topical, parenteral, oral, intranasal, eye drop, intravenous, intramuscular, subcutaneous, or any other suitable means. The dosage administered may be dependent upon the age, weight, kind of concurrent treatment, if any, and nature of the cranial fluid dysfunction. The compounds useful in the method of the present invention may be employed in such forms as eye drops for topical administration, capsules, liquid solutions, suspensions, or elixirs, for oral administration, or sterile liquid forms such as solutions or suspensions for parenteral administration. Any inert carrier is preferably used, such as saline, or phosphate-buffered saline, or any such carrier in which the compounds used in the method of the present invention have suitable solubility properties for use in the method of the present invention.

Typical dosages will vary with the potency of the drugs for activating guanylate cyclase or inhibiting PDE. For eye drop preparations of guanylate cyclase activators or PDE inhibitors, 0.01%–2.0% (gm/100 ml) is typical. For oral organic nitrate guanylate cyclase activators, doses are typically 0.1–30 mg. For oral PDE inhibitors, doses are typically 0.1–300 mg. For i.v. organic nitrate guanylate cyclase activators, doses are typically 0.1–50 μg/min. For atriopeptin analogues, doses vary from 0.1 μg–1.0 mg.

Having now generally described the invention, the same may be further understood by reference to the following examples, which are not intended to be limiting unless so expressly stated.

EXAMPLE 1

Figure 1A:
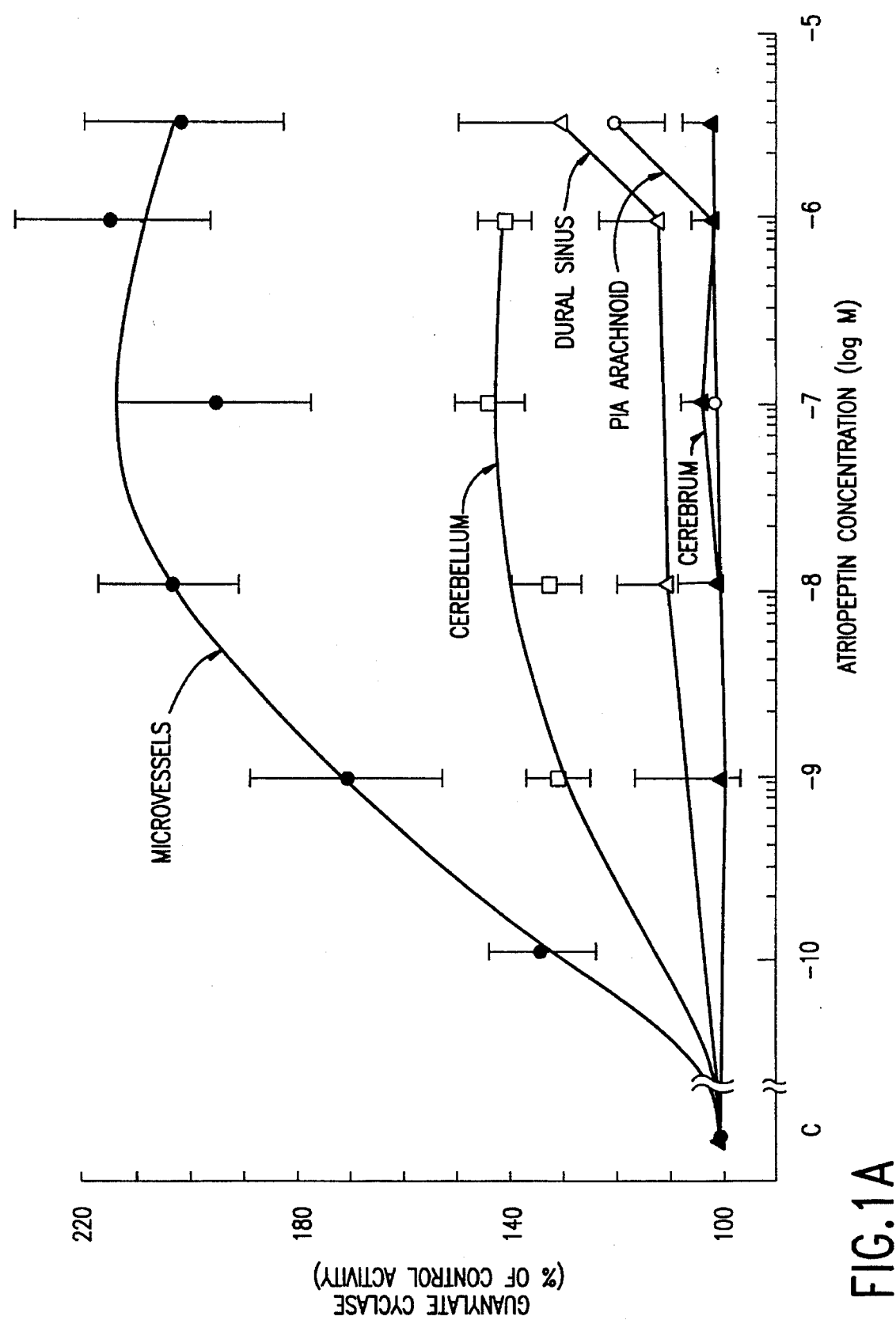
Figure 1B:
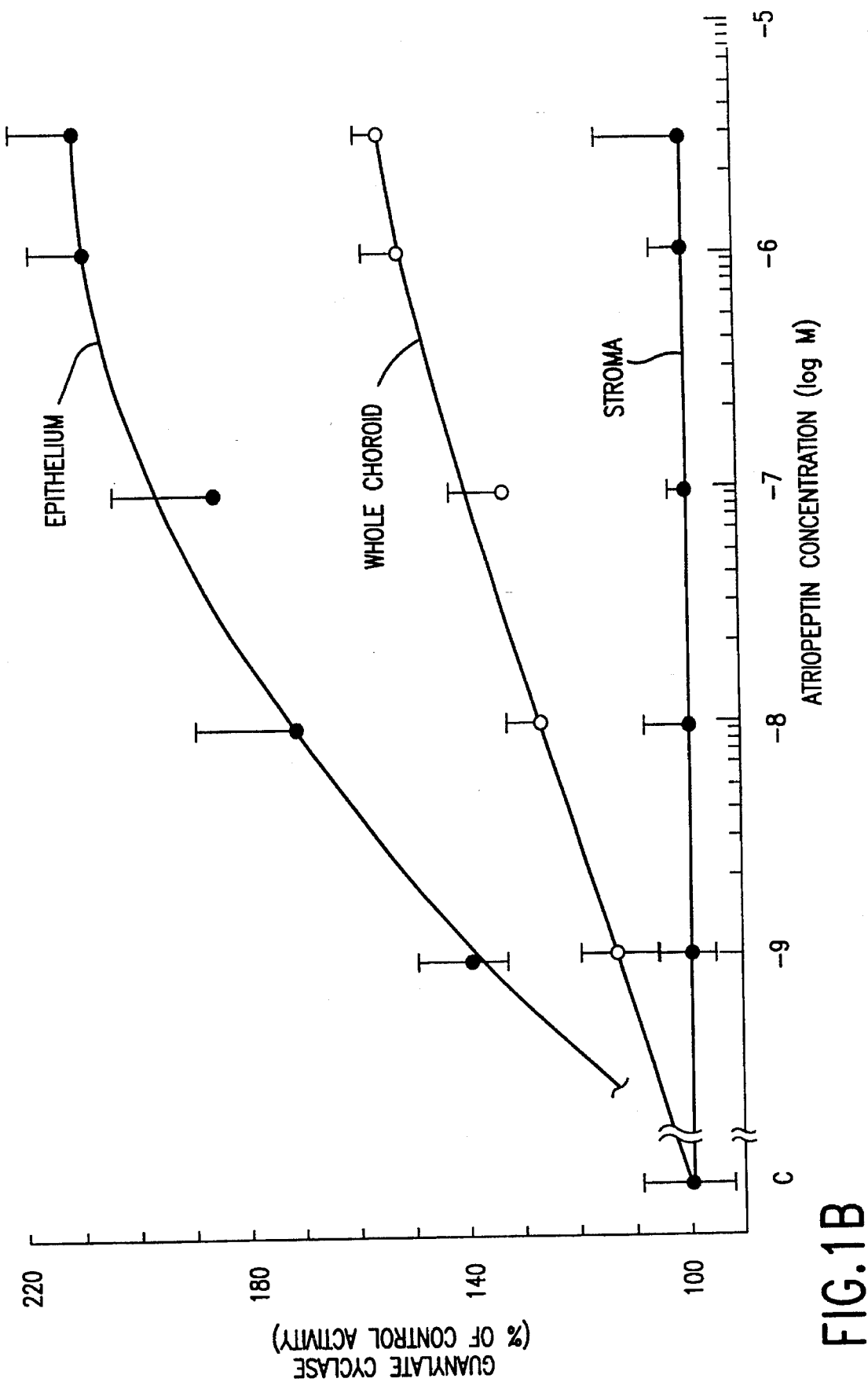

The effect of rANP on membrane-bound guanylate cyclase and adenylate cyclase activity in various brain-barrier tissues and tissue fractions from rabbit was compared with its activity in cerebrum and cerebellum. Guanylate cyclase was measured as the rate of cyclic GMP formation by modifications of the technique of Waldman et al., supra, incorporated herein by reference. Briefly, tissues were homogenized (10 mg wet weight per milliliter) in 50 mM tris-HCl, pH 8.0, 1 mM EDTA, 1 mM dithiothreitol, and 250 mM sucrose and centrifuged at 100,000 g to obtain a P1 pellet. Reaction tubes contained (in 0.3 ml), 50 mM tris, pH 7.6, 6 mM $MnCl_2$, 0.5 mM 3-isobutyl, 1-methylxanthine (IBMX), 10 mM theophylline, 3 mM GTP, hormone (in 0.03 ml containing 2.5 mM ascorbic acid and 0.1% bovine serum albumin), and 0.06 ml of P1 fraction (40 to 60 ug of protein). The reaction (4 minutes at 30° C.) was started by addition of GTP and terminated by addition of 0.3 ml of 150 mM sodium acetate (pH 4.0) and boiling for 3 minutes. Cyclic GMP formed was subsequently measured by radioimmunoassay as described in example 6, infra. Under these conditions, guanylate cyclase activity was linear with time and tissue concentration. Adenylate cyclase activity in P1 fractions was measured according to the method described by Nathanson, et al., *Science;* 204:843 (1979); *Mol. Pharmacol.* 18:199 (1980), see FIG. 1C. FIG. 1B demonstrates choroid epithelial cells isolated according to the method described by Gabuzola, et al., *Soc. Neurosci. Abstr.,* 10:899 (1984); Nathanson, et al., *Soc. Neurosci. Abstr.,* 12:1257 (1986), incorporated herein by reference, but with a lower concentration (0.025%) of trypsin and a rotating tissue tumbler which allowed cleaner fractionation of epithelial cells from erythrocytes and vascular components. In FIG. 1A large stimulations were observed in fractions highly enriched in intraparenchymal cerebral microvessels compared with little or no stimulation in ventral portion of dural sinus (containing arachnoid villi), in pia arachnoid membrane, and in cerebrum. Membrane fractions from cerebellum showed a moderate amount of stimulation. The presence of atriopeptin-activated guanylate cyclase in cerebral microvessels suggests a role for atriopeptins in regulating cerebral water since these microvessels are the site of the blood-brain barrier.

Figure 1C:
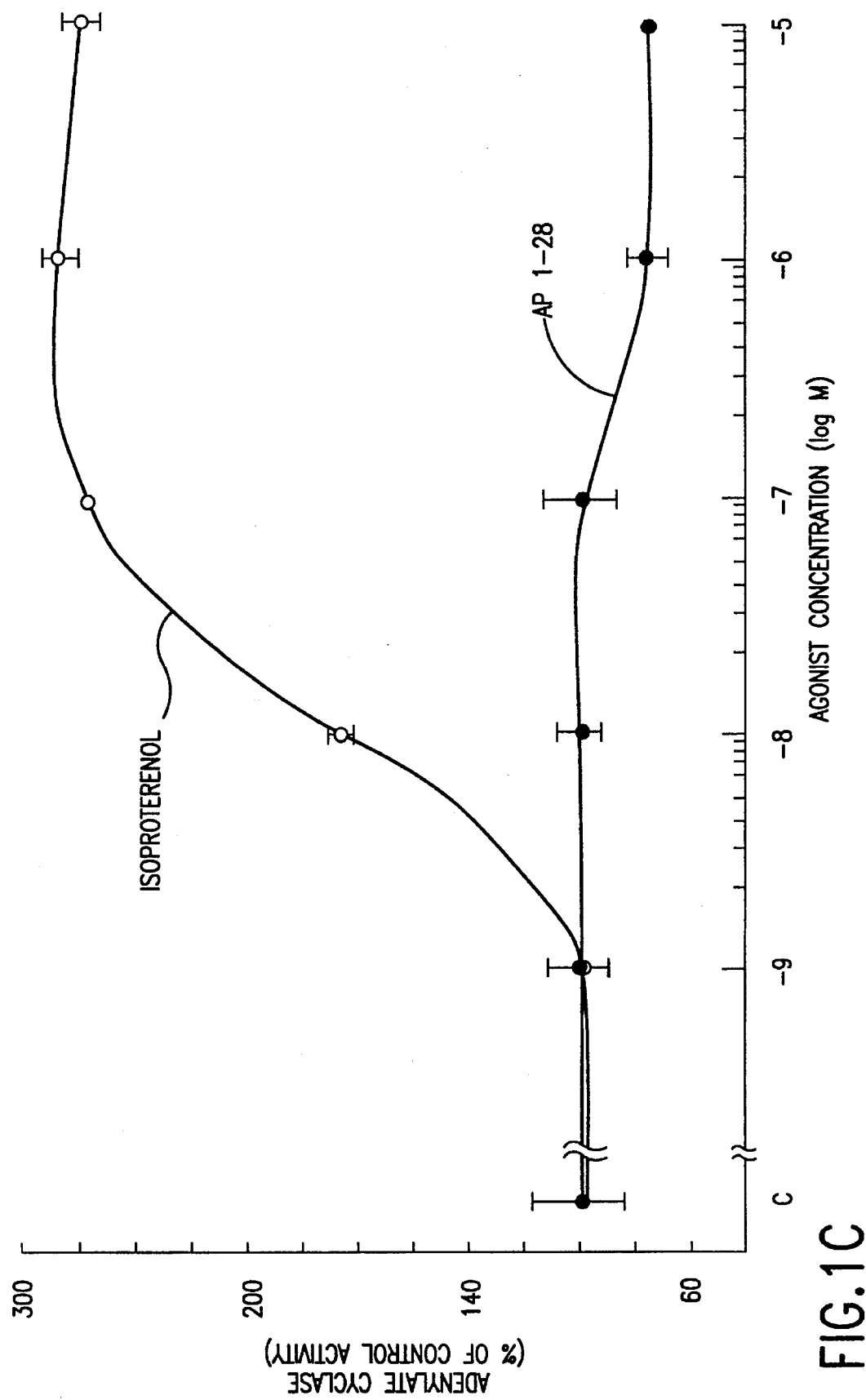
Figure 2C:
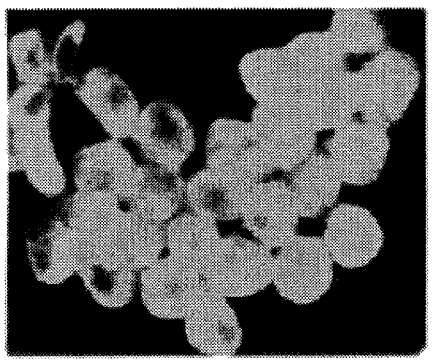
FIGS. 2A, 2B, 2C, 2D, 2E and 2F show the appearance and hormone responsiveness of intact isolated and purified choroid epithelial cells.
Figure 2F:
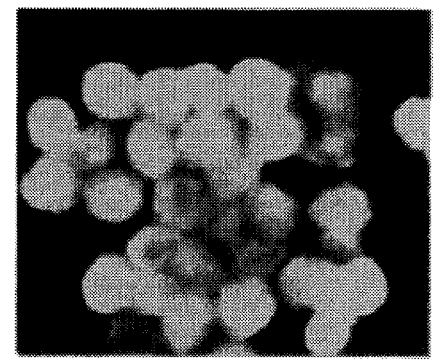
Figure 2B:
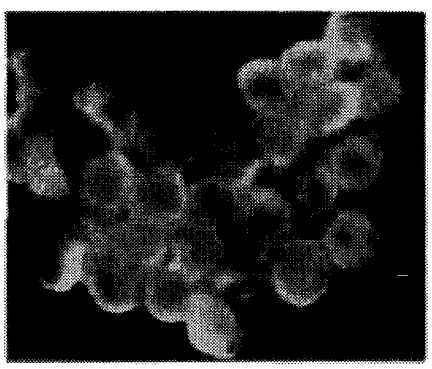
Figure 2E:
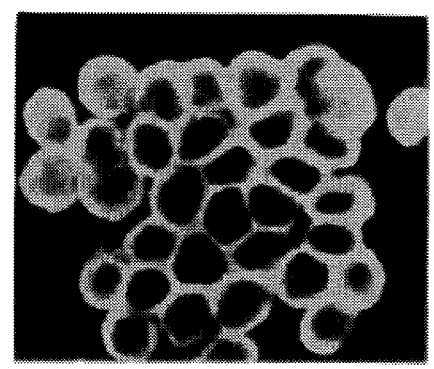
Figure 2A:
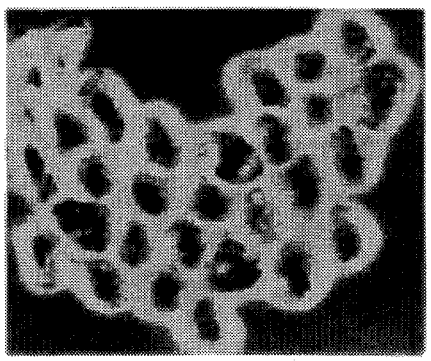

FIG. 1B shows that rat ANP also activated guanylate cyclase in membrane fractions from whole choroid plexus (middle curve). Fractionation of choroid indicated that purified choroid epithelium (site of the blood-CSF barrier) contained most of the rANP receptors, with few present in choroid stroma which contains vascular elements. FIG. 1C demonstrates that the rat ANP stimulation in whole choroid was selective for guanylate cyclase and not adenylate cyclase, causing a small inhibition of the latter enzyme. Adenylate cyclase activity could be stimulated by isoproterenol through β-adrenergic receptors known to be present in this tissue. Values shown are the mean±range for duplicate enzyme determinations, each assayed for cyclic AMP or cyclic GMP in triplicate. For the results shown in FIG. 1, highly enriched suspensions of choroid epithelial cells from intact choroid were prepared and the identity of the cells was confirmed through immuno-histochemical studies showing the presence (>95%) of morphologically typical epithelial cells strongly stained with a polyclonal antibody to the peripheral form of Na- and K-activated adenosine triphosphatase (Na, K-ATPase) Sweadner, et al., *J. Biol. Chem.,* 260:9016 (1985), which only faintly labels endothelial and stromal cells, and with antibody to the protein, DARPP-32, which solely labels epithelial cells (FIG. 2A–2C). Nestler et al., *Science,* 225:1357 (1984). When isolated as described hereinabove, the choroid epithelium is a nearly homogenous population of cells that can be identified by cell markers and sustained in short-term culture. Stimulation by rANP was selective for guanylate cyclase and did not activate adenylate cyclase in the same brain-barrier preparations, although adenylate cyclase was stimulated by isoproterenol (FIG. 1C). As shown in FIG. 1C, high concentrations of rANP caused a small inhibition of adenylate cyclase. Stimulation of guanylate cyclase in barrier tissues was also selective for the intact 28-amino acid peptide. Thus, in choroid plexus, rANP fragment 1–11 was about 10% to 15% as active as the intact peptide and rANP fragment 13–28 caused almost no stimulation of guanylate cyclase, a pattern of activity nearly identical to that found in rabbit kidney. For rANP 1–28, the range of $K_a$ values (0.5 to 10 nM) that was observed for guanylate cyclase activation in cerebral microvessels and choroid plexus was similar to the range of binding affinities (0.1 to 2 nM) reported in other tissues for radiolabeled atriopeptins. FIG. 1a shows that rat atrial natriuretic peptide (rANP) 1–28 [Ser-Leu-Arg-Arg-atriopeptin III (APIII)] was a potent activator of guanylate cyclase activity in purified rabbit cerebral microvessels [maximum velocity of enzyme activity ($V_{max}$), 215% of control; activation constant ($K_a$), 0.5 nM]. From other studies, it is known that such microvessels consist of a high percentage of endothelial cell-containing cerebral capillaries. A similar degree of activation of guanylate cyclase by rANP was observed in microvessels prepared from pig brain.

FIG. 1B (middle curve) shows that rANP also stimulated enzyme activity in membrane fractions prepared from whole rabbit choroid plexus obtained from lateral, third, and fourth ventricles. In five separate experiments, the $K_a$ for activation of the enzyme in the choroid (9.8±5.1 nM; SEM) was similar to that ($K_a$=5±2 nM; SEM, N=4) observed in rabbit kidney, a tissue known to be rich in atriopeptin receptors, and somewhat greater than that observed for atriopeptin stimulation in the rabbit cerebellum (FIG. 1A), a tissue known to be enriched (relative to other brain areas) in cyclic GMP. The $V_{max}$ for stimulation of basal activity in the choroid plexus averaged 58%±16% (SEM, N=5).

However, no stimulation of guanylate cyclase activity in membrane fractions prepared from rabbit or pig cerebral cortex occurred (FIG. 1A). In membranes prepared from the ventral portion of pig or rabbit superior sagittal dural sinus, which contains arachnoid villi, rANP caused a small stimulation of guanylate cyclase but only at high concentrations ($K_a$>1000 nM). There was also a very small (15%) degree of enzyme stimulation in the pia-arachnoid, a preparation consisting of both pia-arachnoid membrane and small extraparenchymal cerebral arterioles and veins.

EXAMPLE 2

Figure 2D:
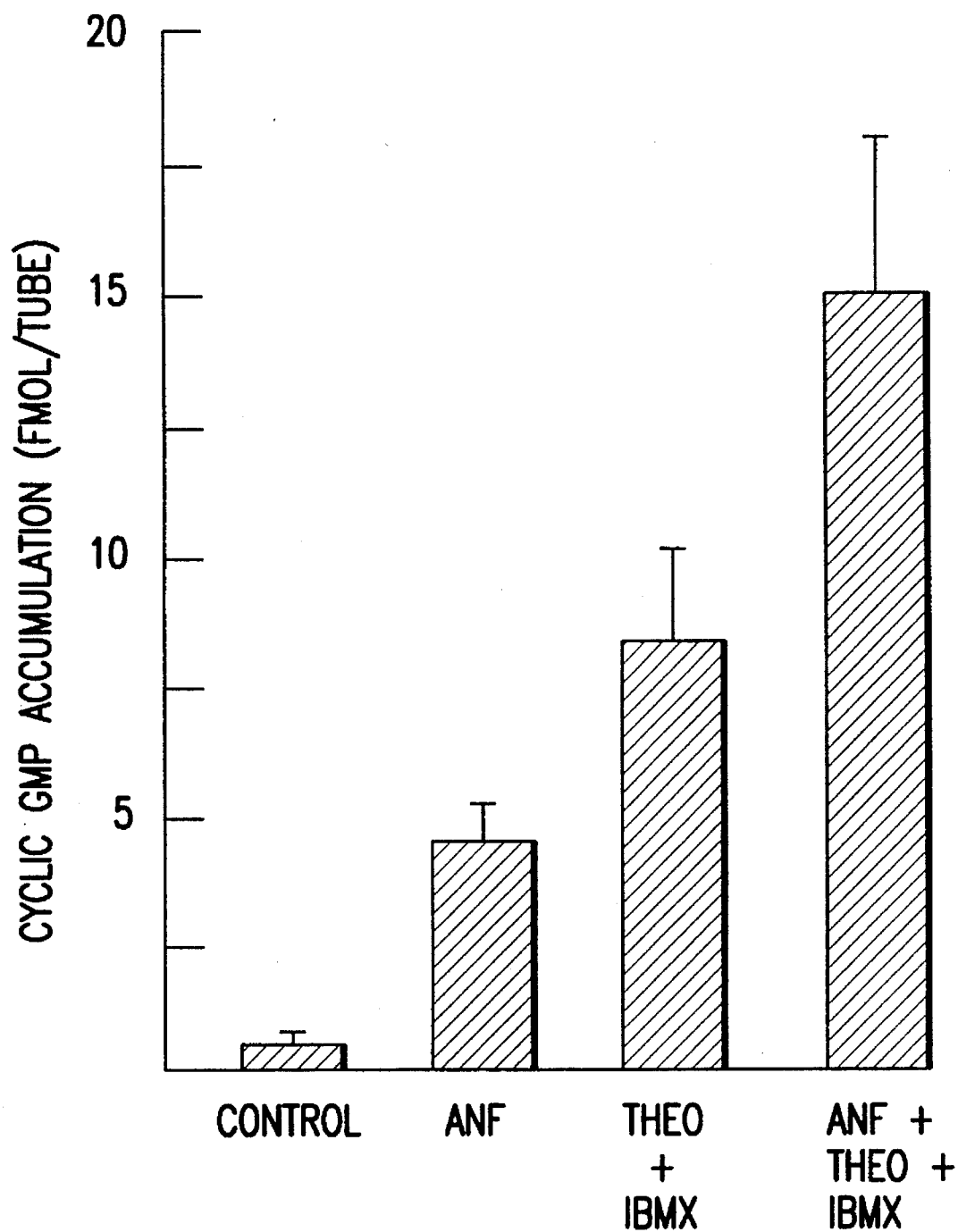

Purified secretory epithelial cells were isolated and maintained in tissue culture medium in the absence of any hormones. After 3 hours, rANP was added either alone or in the presence of phosphodiesterase (PDE) inhibitors to a suspension of choroid epithelial cells incubated at 37° C. in artificial CSF. FIG. 2A demonstrates the appearance by phase contrast microscopy of a small group of epithelial cells after isolation and purification. FIG. 2B shows the same cells as in FIG. 2A which have been stained with a rabbit polyclonal antibody (1:150 dilution) to the alpha form of Na,K-ATPase, Sweadner et al., *J. Biol. Chem.*, 260:9016 (1985) followed by second antibody (1:100 dilution). Plasma membrane fluorescence (see also FIG. 2E) was characteristic of choroid epithelium as demonstrated with rhodamine optics. FIG. 2C shows epithelial cells which were also immunostained with mouse monoclonal antibody to DARPP-32, Nestler et al., *Science,* 225:1357 (1984), followed by second antibody (1:100 dilution). More diffuse staining was found only in epithelium and not in vascular or stromal components of choroid epithelial cells as determined by fluorescein optics. FIG. 2D shows a suspension of choroid epithelial cells incubated at 37° C. in artificial CSF. After exposure for 5 minutes to 1 μM rANP, the cells showed a marked increase in intracellular cyclic GMP content, an effect that was potentiated by the phosphodiesterase inhibitors theophylline (10 mM) and IBMX (0.5 mM). The synergistic effect of phosphodiesterase inhibitors and rANF is demonstrated in FIG. 2D where the cGMP accumulation after treatment with the combination is greater than would be expected from the summation of the effects of phosphodiesterase inhibitors and rANF added individually. For one experiment, the mean±range is shown for duplicate determinations, each assayed in triplicate for cyclic GMP content. In four separate experiments, the degree of stimulation by rANP alone varied from 290% to 1460%. FIG. 2E demonstrates another group of epithelial cells showing bright plasma membrane immunostaining of Na,K-ATPase. FIG. 2F shows the same cells immunostained with antibody to DARPP-32. Fewer than 5% of cells were DARPP-negative.

After exposure for 5 minutes to 1 μM rANP the cells showed a marked increase in intracellular cyclic GMP content, an effect that was potentiated by the phosphodiesterase inhibitors theophylline (10 mM) and IBMX (0.5 mM). For one experiment, the mean±range is shown for duplicate determinations, each assayed in triplicate for cyclic GMP content. In four separate experiments, the degree of stimulation by rANP alone varied from 290% to 1460%. After the cells were incubated for 5 minutes, they were killed and their cyclic GMP content was determined. The isolated epithelial cells showed more than an eightfold increase in cyclic GMP content when incubated with rANP alone (FIG. 2D). Basal cyclic GMP content was increased by the PDE inhibitors, and the combination of rANP and PDE inhibitors caused more than 30-fold increase in cyclic GMP content. (similar but somewhat larger increases were seen after 15 minutes of incubation.) These marked increases in cyclic GMP provide further evidence that the choroid epithelium is an atriopeptin end organ.

EXAMPLE 3

Figure 3:
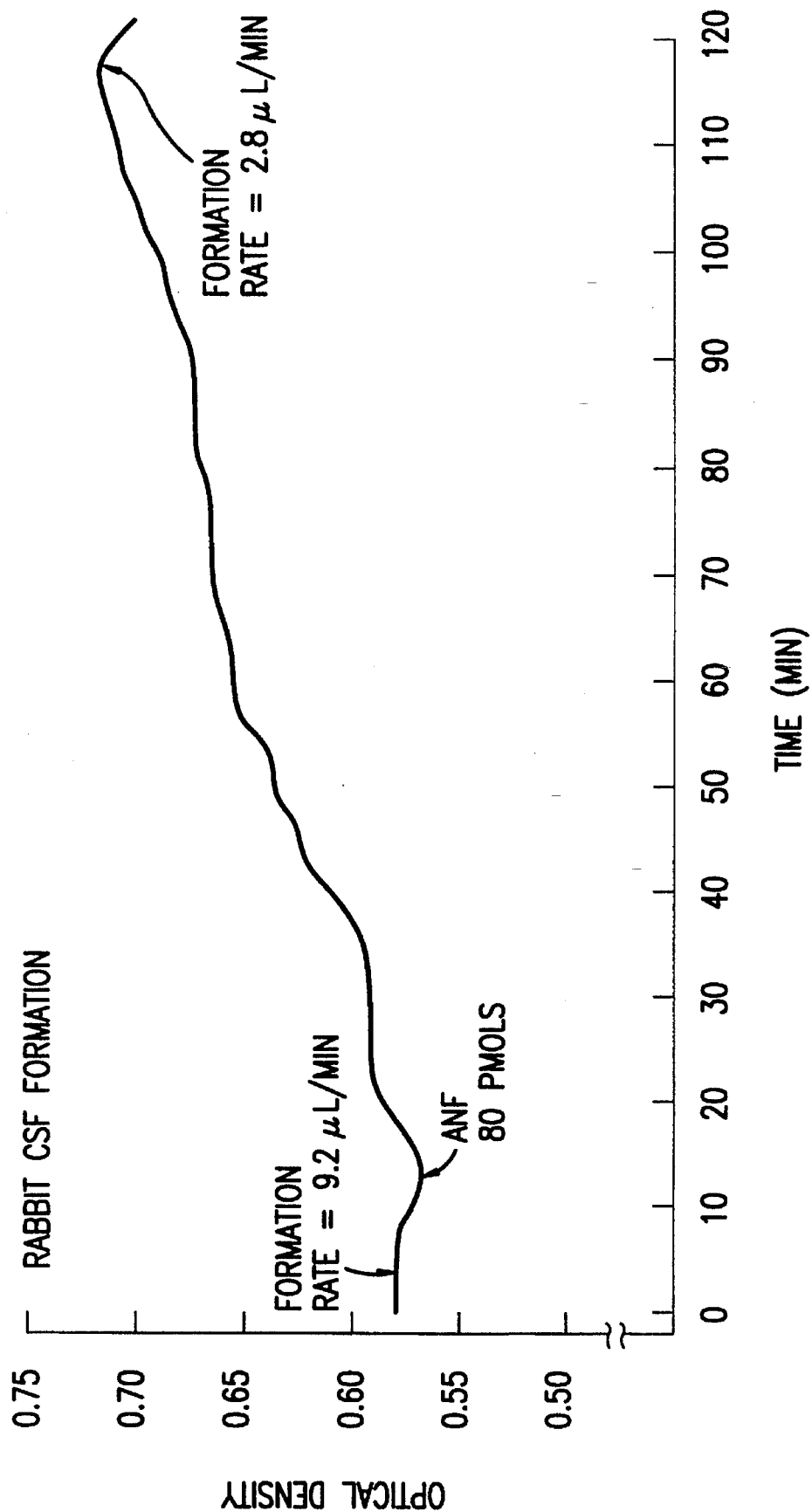
FIG. 3 shows the inhibitory effect of intraventricular administration of rANP on CSF production rate in a rabbit with chronically implanted lateral ventricular and cisternal catheters. The increase in optical density shown indicates a decrease in the rate of fluid production.

The effects of rANP on CSF production measured by ventricular-cisternal perfusion in living rabbits demonstrated that atriopeptins affect the secretory function of these cells, which produce CSF as shown on FIG. 3. Drug was given intraventricularly, either by bolus injection or by continuous addition (during a 10-minute period) to the CSF perfusion system. Ventricularcisternal perfusion of Blue dextran was carried out by a closed system with active pumping both into and out of the catheters at a rate of 30 l/min. Output dye concentration was monitored continuously with an in-line photocell; and a separate, contralateral ventricular catheter independently measured intracranial pressure. Positive responses were observed in 13 of 14 experiments, in 3 of which rANP (30 pmol) was given by bolus intraventricular injection and in 10 of which rANP was given by continuous intraventricular infusion at 3 to 30 pmol/min for 10 minutes. Drug was administered in an artificial CSF containing 0.01% rabbit serum albumin (RSA) and 0.25 mM ascorbate. In addition, all plastic surfaces were pretreated with 0.1% RSA to reduce peptide loss by adsorption. Out of 14 rabbits in which CSF production could be adequately assessed throughout the experiment, 13 showed a decrease in the rate of CSF production. In one animal, there was no change in CSF secretion rate, and in no case was there an increase in CSF production. FIG. 3 shows a positive response to a bolus injection of 30 pmol of rANP into the lateral ventricle. During a period of 100 minutes, secretion rate dropped by 70%. In the 13 positive responses, the mean decrease observed was 35.3%±6.9% (SEM) from a starting basal CSF secretion of 8.3±0.8 l/min. In other experiments, intravenous injection of similar doses of rANP caused no change in peripheral blood pressure, suggesting that the decreased CSF production rate observed was not due to a systemic effect on vascular perfusion pressure.

EXAMPLE 4

Ciliary process tips were obtained from male, 3–4 kg, New Zealand white rabbits, immediately following sacrifice with an overdose of ether, as described in Nathanson, *Invest. Ophthal. Vis. Sci.*, 21:7981 (1982). The tissue was minced and homogenized (10 mg/ml) by hand in a glass-glass homogenizer in a buffer consisting of 50 mM Tris HCl, pH 8.0; 1 mM EDTA, and 250 mM sucrose. The homogenate was diluted 30-fold with buffer and centrifuged at 100,000× g, to obtain a P1 fraction. The pellet was rehomogenized in the original volume and left on ice until use. P1 fractions were also prepared from wedges of rabbit kidney taken from the same animals. In some experiments, P1 fractions were prepared from iris and from ciliary body, as described in Nathanson, *Proc. Natl. Acad. Sci. USA*, 77:7420 (1980). Briefly, iris was removed from its attachment to the ciliary body, cleaned of adhering ciliary process tissue, washed, and homogenized as above. The ciliary muscle was cleaned of most remaining ciliary process tissue, freed from the underlying sclera by blunt and sharp dissection, and then washed and homogenized.

EXAMPLE 5

Atriopeptin-activated guanylate cyclase activity was measured as the rate of conversion of GTP to cyclic GMP. For this assay, reaction tubes were prepared to contain (in 0.3 ml final volume): 50 mM Tris HCl, pH 7.6; 6 mM $MnCl_2$; 1 mM 3-isobutyl-1-methylxanthine (IBMX); 10 mM theophylline; 3 mM GTP; hormone (in 0.03 ml containing 2.5 mM ascorbic acid and 0.1% rabbit serum albumin); and tissue P1 fraction (0.06 ml). The reaction was started by the addition of GTP. Tubes were incubated for 4 min at 30° C., and the reaction stopped by addition of 0.3 ml of 150 mM sodium acetate (pH 4.0), followed by boiling for 3 min. Under these conditions, guanylate cyclase activity was linear with respect to time and tissue concentration.

EXAMPLE 6

The cyclic GMP was typically measured by radio-immunoassay (RIA) using a polyclonal antibody (NEX137, New England Nuclear Corp.). This polyclonal antibody has both a great deal of sensitivity (ED50 of 25 fmoles at final dilution) as well as selectivity (less than 0.03% crossover with cyclic AMP). This degree of selectivity for cyclic GMP, coupled with the finding that the specific activity of ciliary process guanylate cyclase is quite high (Table 1), indicated that there was no significant cross-contamination of guanylate cyclase activity with adenylate cyclase activity.

For RIA, each tube contained (in 0.5 ml), 50 mM sodium acetate buffer (pH 6.2), 2 mM EDTA, 1 mg/ml bovine serum albumin, 0.1 ml of sample (or diluted sample), 8,000–15,000 cpm (about 5 fmole) of $^{125}I$ succinyl cyclic GMP tyrosine methyl ester, and antibody to bind 25–35% of the label. Prior to the addition of label and antibody, sample tubes underwent an acetylation reaction with acetic anhydride and triethylamine, according to the method of Harper and Brooker, *J. Cyclic Nucl. Res.*, 1:207 (1975) in order to increase the sensitivity of the assay. (Acetyl-cyclic GMP has a greater affinity for the antibody than cyclic GMP). After addition of label and antibody, the mixture was incubated at 4° C. for 24–48 hours, then the binding reaction terminated by addition of 0.1 ml of a mixture of 1 gm/10 ml of Norit XG charcoal in 50 mM sodium acetate buffer (pH 6.2) containing 0.2 g/10 ml of bovine serum albumin. (The charcoal-BSA-buffer were pre-mixed for 1 hr prior to addition). The mixture was vortexed, allowed to stand for 10 min at 4° C., then centrifuged at 2000×g for 30 minutes and an aliquot of the supernatant taken for measurement of bound cyclic GMP. Using these conditions, the assay was sensitive over the range of 2.5 to 500 femtomoles. Activation constants ($K_a$) were determined from dose-response curves utilizing 12–14 data points (6–7 concentrations of hormone, in duplicate), each point representing the mean of triplicate RIA determinations.

EXAMPLE 7

The measurement of intraocular pressure (IOP), was performed using procedures similar to those described in Nathanson, *Brit. J. Pharmacol.*, 73:97 (1981) and Nathanson, *Current Eye Res.*, 4:191 (1985). Briefly, male (3–5 kg), New Zealand white rabbits were housed under standard conditions and exposed to a 12 hr light-dark cycle. IOP was measured with a Perkins applanation tonometer after topical anesthesia with 0.4% benoxinate (and 0.25% sodium fluorescein). The tonometer had been calibrated previously by connecting the anterior chamber of enucleated rabbit eyes to a manometer (and reservoir) and taking tonometer readings at different pressures. A number of preliminary IOP readings were made in order to accommodate the animals to the measurement procedure. Readings were then taken just prior to drug or vehicle injection and at 3, 9, 20, 27, 44, 51, 72, and 144 hours post-injection.

Following topical anesthesia with 0.4% benoxinate, rabbits received rat atrial natriuretic peptide 1–28 (rANP) via a 10 microliter, intravitreal injection, through a 30 g ½" needle, the tip of which was positioned at the approximate center of the eye. Drug was dissolved in a solution of artificial aqueous humor containing (in mmol/liter): NaCal 130, KCl 2.7, $NaH_2CO_3$ 18.3, $MgCl_2$ 1.33, $CaCl_2$ 1.5, Glucose 10, HEPES 20, and L-ascorbic acid, 2.5. The contralateral eye received a 10 microliter injection of vehicle alone. In order to evaluate the possible effects of intravitreal injection, per se, on IOP, additional rabbits received a 10 microliter intravitreal injection of vehicle in one eye only.

EXAMPLE 8

Atriopeptin-activated guanylate cyclase activity was measured, as described in Example 5, in membranes from rabbit kidney and ciliary process prepared as in Example 4.

In particulate fractions of rabbit kidney, guanylate cyclase activity was present at high specific activity and could be activated by rANP at low concentrations. In four separate experiments, the $K_a$ for hormone activation ranged from 1 to $9 \times 10^{-9}$M, with a $V_{max}$ which varied from 63 to 151% stimulation of basal activity. FIG. 4 shows a typical response. Values shown in FIG. 4 are the means±range for duplicate guanylate cyclase determinations, each assayed by radioimmunoassay (RIA) in triplicate. Control activity was 7.1 pmol/mg protein/min.

In the rabbit ciliary process, guanylate cyclase in P1 fractions was extremely active, with basal levels (49.4±12.7 pmol/mg protein/min; ±SEM, N=4 separate experiments) considerably exceeding that found in kidney (10.3±2.5 pmol/mg protein/min; N=4). This high concentration of guanylate cyclase activity also exceeded that (20.4±4.3; N=5) which previously reported for choroid plexus and for other atriopeptin receptor tissues.

In addition, at very low concentrations, rANP caused significant stimulation of basal guanylate cyclase activity in ciliary process (FIG. 5). In four separate experiments, the $K_a$ for hormone stimulation of the enzyme ranged from 0.4 to $4\times10^{-9}$M, with a $V_{max}$ which varied from 24 to 337% stimulation of basal activity. This range of activation is similar, also, to the values obtained from studies of the vasorelaxant properties of atriopeptins in rabbit aorta, where the $EC_{50}$ for Arg-Arg-APIII has been reported to range from $1\times10^{-10}$ to $1\times10^{-9}$M.

Table 1 shows that activation of ciliary process guanylate cyclase by rANP was selective for the complete peptide; rANP fragment 13–28 showed partial activity and rANP fragment 1–11 was almost devoid of activity.

TABLE 1

Stimulation of Guanylate Cyclase Activity By Intact rANP 1–28 and By Atriopeptin Fragmants 1–11 and 13–28

| Peptide | Vmax Stimulation (%) of Guanylate Cyclase | |
|---|---|---|
| | Ciliary Process | Kidney |
| rANP 1–11 | 4 ± 6 | 25 ± 6 |
| rANP 13–28 | 51 ± 5 | 54 ± 4 |
| rANP 1–28 | 124 ± 5 | 129 ± 25 |

A complete dose response curve was run for each peptide. The $V_{max}$ values shown are the mean ± range of duplicate determinations, each assayed by RIA in triplicate.

In tissue distribution studies, the greatest hormone-stimulated activity was in the isolated ciliary processes. Ciliary body and iris showed significantly less rANP-stimulated activity.

This distribution of activity is similar to that reported for $beta_2$-adrenergic receptors associated with the activation of adenylate cyclase.

EXAMPLE 9

This example demonstrates the effects of exogenous rANP on intraocular pressure. FIG. 6 shows the effects of unilateral intravitreal injection of 0.3 nmoles of rANP (1–28) on intraocular pressure in a group of eight albino rabbits. The contralateral eye received intravitreal injection of vehicle alone. Over a period of 9 hours, the ipsilateral eyes underwent a marked decline in pressure of about 5 mm (Hg). This degree of hypotension persisted until about 48 hours post-injection and then underwent a slow recovery over the following four days. The decrease in pressure, compared with pre-injection IOP, was statistically significant at all time points from 3 to 72 hours post-injection. Values shown are mean±SEM. Filled circles represent the IOP in the ipsilateral eye; open circles represent the IOP in the contralateral eye. *($p<0.05$); **($p<0.01$), for paired Students T-test relative to preinjection pressure (time 0). The IOP at 3, 9, 20, 27, 44, and 51 hours was also significantly decreased relative to the pressure present at the same time in the contralateral, vehicle-injected eyes. During the entire period, no affect on pupillary diameter of either the ipsilateral or contralateral eye was noted.

Following injection of rANP in the ipsilateral eye, IOP in the contralateral, vehicle-injected eye also showed a decrease, although it was smaller, of somewhat slower onset, and recovered by 72 hours. This contralateral decrease was statistically significant ($p<0.05$ vs. pre-injection IOP) at 20 and 44 hours following injection. The dose of rANP which caused a marked and prolonged decrease in ipsilateral IOP, if distributed uniformly within a sphere the size of a rabbit eye, would yield a concentration ($2-3\times10^{-7}$M) similar to that which caused maximal stimulation of ciliary process guanylate cyclase activity (FIG. 5).

EXAMPLE 10

A separate group of 5 rabbits received a unilateral intravitreal injection of vehicle alone in order to evaluate the possible effects of intravitreal injection, per se, on IOP. FIG. 7 shows that there was no significant decrease in IOP, relative to starting IOP, at any of the time points observed, in either the ipsilateral (injected) or contralateral (non-injected) eye; nor, at a given time point, was there any significant difference between ipsilateral and contralateral eyes. At 9 hours (the only measurement made during the normal dark cycle of the rabbits) there was a small, non-significant increase in IOP. Also, on a given day, afternoon measurements of IOP tended to be somewhat higher than morning measurements. These small daily changes may have been due to a circadian effect.

EXAMPLE 11

Inhibitors of PDE also cause a decrease in intraocular pressure in rabbit eye.

A potent PDE inhibitor of the arylxanthine class, 1,3-dibutylxanthine, was applied unilaterally and topically to rabbit eyes in a 0.5% solution. There was a small decrease in the IOP in the contralateral eye, possibly due to systemic leakage. The IOP was decreased 4 mm (Hg) in the ipsilateral eye (FIG. 8). This example demonstrates that inhibition of the enzyme which hydrolyzes cGMP mimics the reduction in IOP caused by atriopeptins.

EXAMPLE 12

FIG. 9A shows the effect of topical administration of another PDE inhibitor, 1-methyl-3-isobutylxanthine on IOP. Again there was about a 4 mm (Hg) decrease in intraocular pressure. FIG. 9B shows the effect of 1-methyl-3-isobutylxanthine on inhibiting cGMP phosphodiesterase in ciliary process. This xanthine inhibited the enzyme with an $IC_{50}$ (concentration necessary for 50% enzyme inhibition) of 25 uM.

EXAMPLE 13

FIG. 10 shows that 1,2,3-propanetriol trinitrate (1,2,3-PTT), i.e., nitroglycerine, activates guanylate cyclase in the ciliary process of the rabbit. Experimental procedures set forth in Example 1 were repeated, substituting nitroglycerine for rANP and using a crude broken-cell preparation as opposed to a washed-membrane preparation. The results demonstrate that nitroglycerine caused a significant stimulation of basal guanylate cyclase activity in the ciliary process at low concentrations.

EXAMPLE 14

The effect of nitroglycerine eye drops on rabbit intraocular pressure was also measured. The IOP of 8 conscious, male albino rabbits (3–4 kg) was measured by applanation pnumatonometry after topical anesthesia with 0.4% benoxinate. Nitroglycerine in phosphate buffered saline, pH 7.4, was given unilaterally, in two 25 µl drops spaced five minutes apart. Blood pressure and pulse rate were measured by a photoelectric detector using an automated external tail cuff. FIG. 11 shows the results of the topical administration of a 0.03% (gm/100 ml) nitroglycerine solution on IOP. A marked decrease in IOP (5.2 mm Hg at maximum), which was greatest at one hour and still significantly reduced at six hours, can be seen. By 24 hours, pressure had returned to normal. Importantly, there was no significant change in pulse rate or in systolic, diastolic or mean blood pressure, as can also be seen in FIG. 12.

As FIG. 13 illustrates, higher doses of nitroglycerine caused no additional decrease in IOP, and lower doses were less effective. Each curve demonstrates the±mean of eight rabbits at various times after administration of 50 µl eye drops containing nitroglycerine in neutral aqueous solution at the dose shown. At higher doses, contralateral eyes also showed a decrease in pressure, although significantly less, ranging from 40–75% of that seen ipsilaterally. At no dose did conjunctiva inflammation nor any change in pupillary diameter occur. At higher doses (0.1%), there was a slight, transient (five minutes) hyperemia of the conjunctiva vessels.

This experiment indicates that direct topical ocular administration of a guanylate cyclase activator as an eye drop can decrease IOP without any significant change in systemic cardiovascular parameters. Thus, administration of nitroglycerine as an eye drop involves a more selective delivery to end organ tissues in the eye.

EXAMPLE 15

The effect of administration of a nitroglycerine eye drop preparation (50 µl of 0.1% aqueous solution in one eye) in a volunteer human is illustrated in FIG. 14. IOP was measured by applanation pneumatonometry and blood pressure and pulse were measured by arm cuff. Topical administration of nitroglycerine significantly decreased IOP by formula mmHg without change in systemic blood pressure (shown) or pulse (not shown).

EXAMPLE 16

The inventor has found a number of other compounds which also increase guanylate cyclase and decrease IOP when applied as an eye drop.

As Table 2 indicates, minoxidil (Compound "M") also increases guanylate cyclase activity alone, and to an even greater extent when combined with rANP. FIG. 15 illustrates the effect of a 50 µl of 0.1% aqueous solution of minoxidil on intraocular pressure in 12 rabbits. Minoxidil caused a significant decrease in IOP.

TABLE 2

| CILIARY PROCESS GUANYLATE CYCLASE ACTIVITY (Percent Increase) | |
| --- | --- |
| COMPOUND "M" ($10^{-4}$M) | 14 ± 4 |
| rANP 1–28 ($10^{-6}$M) | 60 ± 27 |

TABLE 2-continued

| CILIARY PROCESS GUANYLATE CYCLASE ACTIVITY (Percent Increase) | |
| --- | --- |
| COMPOUND "M" + rANP | 210 ± 22 |

As Table 3 indicates, another compound, sodium nitrate (Compound "N") was found to increase ciliary process guanylate cyclase activity and FIG. 16 illustrates the effect of sodium nitrite as 50 µl in a 0.1% eye drop preparation. Experimental procedures were similar to those described in Example 14. Sodium nitrite lowers IOP in rabbits.

TABLE 3

| CILIARY PROCESS GUANYLATE CYCLASE ACTIVITY (Percent Increase) | |
| --- | --- |
| COMPOUND "N" | 46 |
| rANP 1–28 | 74 |

Finally, hydralazine, a drug thought to work through activation of guanylate cyclase activation, when given to rabbits as a 0.1% eye drop preparation in normal saline, decreases IOP. Experimental procedures used were similar to those described in Example 14. FIG. 17 illustrates this effect.

Having now fully described the invention, it may readily be seen by those of skill in the art that the present invention can be performed utilizing equivalent agents without affecting the scope of the invention or any embodiment thereof.

I claim:

1. A method of treating glaucoma in an individual, comprising topically administering a therapeutically-effective amount of hydralazine to said individual.

2. The method of claim 1 wherein said individual is an animal.

3. The method of claim 2 wherein said animal is a human.

4. The method of claim 1 wherein said hydralazine comprises a 0.01–0.5% solution.

5. A method of treating glaucoma in an individual, comprising topically administering a therapeutically-effective amount of an inorganic-cation-containing, non-toxic, water soluble, non-organic nitrite to said individual.

6. A method of treating glaucoma in an individual, comprising systemically administering a therapeutically effective amount of an inorganic-cation-containing, non-toxic, water soluble, non-organic nitrite to said individual.

7. A method of treating glaucoma in an individual, comprising administering a therapeutically-effective amount of minoxidil to said individual.

8. The method of claim 7 wherein said administration is topical.

9. The method of claim 8 wherein said minoxidil is comprised of a 0.02–2% solution.

10. The method of claim 9 wherein said minoxidil is comprised of a 0.02–0.2% solution.

11. The method of claim 7 wherein said administration is systemic.

12. The method of claim 11 wherein said administration is oral.

13. The method of claim 5 wherein the nitrite is sodium nitrite.

14. The method of claim 6 wherein the nitrite is sodium nitrite.

\* \* \* \* \*